(12) United States Patent
Miller et al.

(10) Patent No.: US 11,333,589 B2
(45) Date of Patent: May 17, 2022

(54) GAS-LIQUID FALLING FILM EQUILIBRATION SYSTEM AND METHODS OF USE

(71) Applicant: Smithsonian Institution, Washington, DC (US)

(72) Inventors: Alexander Whitman Miller, Annapolis, MD (US); Amanda C. Reynolds, Annapolis, MD (US)

(73) Assignee: Smithsonian Institution, Washington, DC (US)

( * ) Notice: Subject to any disclaimer, the term of this patent is extended or adjusted under 35 U.S.C. 154(b) by 0 days.

(21) Appl. No.: 16/980,355

(22) PCT Filed: Mar. 21, 2019

(86) PCT No.: PCT/US2019/023455
§ 371 (c)(1),
(2) Date: Sep. 11, 2020

(87) PCT Pub. No.: WO2019/183411
PCT Pub. Date: Sep. 26, 2019

(65) Prior Publication Data
US 2021/0048378 A1 Feb. 18, 2021

Related U.S. Application Data

(60) Provisional application No. 62/646,357, filed on Mar. 21, 2018.

(51) Int. Cl.
*G01N 1/38* (2006.01)
*G01N 33/18* (2006.01)

(52) U.S. Cl.
CPC ............... *G01N 1/38* (2013.01); *G01N 33/18* (2013.01)

(58) Field of Classification Search
CPC ......... G01N 1/38; G01N 1/4022; G01N 33/18
See application file for complete search history.

(56) References Cited

U.S. PATENT DOCUMENTS

| 3,062,627 | A | 11/1962 | Zuiderweg |
| 3,171,725 | A | 3/1965 | Eckey |
| 5,295,169 | A * | 3/1994 | Tominaga ............... G21C 15/18 376/293 |
| 9,562,837 | B2 * | 2/2017 | Link .................... C12Q 1/6827 |
| 2011/0176987 | A1 | 7/2011 | Haggerty et al. |
| 2012/0231504 | A1 * | 9/2012 | Niazi ........................ F24F 7/06 435/69.4 |

(Continued)

OTHER PUBLICATIONS

International Search Report and Written Opinion, International Application No. PCT/US2019/023455 (published under WO 2019/183411), 13 pages (dated Jun. 7, 2019).

*Primary Examiner* — Francis C Gray
(74) *Attorney, Agent, or Firm* — Hoffmann & Baron, LLP

(57) ABSTRACT

The current disclosure provides a gas-liquid falling film equilibration apparatus, systems incorporating the apparatus, and methods of their use. The apparatus comprises a chamber, an equilibration member within the chamber, liquid and gas inlet and outlets, such that a liquid introduced into the chamber from the liquid inlet contacts the upper portion of the outer surface of the equilibration member. The apparatus finds use in the measurement of dissolved gases in a variety of liquids including the measurement of carbon dioxide in water.

20 Claims, 8 Drawing Sheets

(56) References Cited

U.S. PATENT DOCUMENTS

| | | | |
|---|---|---|---|
| 2016/0251628 A1* | 9/2016 | Vincent | A61K 35/42 424/93.7 |
| 2021/0123936 A1* | 4/2021 | Swanson | G01N 33/24 |

* cited by examiner

GAS-LIQUID FALLING FILM EQUILIBRATION SYSTEM AND METHODS OF USE

CROSS REFERENCE TO RELATED APPLICATIONS

This application is a national stage filing under 35 U.S.C. § 371 of PCT International Application No. PCT/US2019/023455, filed on Mar. 21, 2019, which claims the benefit of U.S. Provisional Application 62/646,357, filed on Mar. 21, 2018, the contents of each of which applications is incorporated herein by reference in its entirety.

TECHNICAL FIELD

Systems and methods for determining the concentration of gases in liquids are provided. The systems include an apparatus (equilibrator) having a high surface area that permits gases present (e.g., dissolved) within the liquid to diffuse into an exchange gas, permitting measurement of the gases. The systems find use in the measurement of a variety of gases including carbon dioxide ($CO_2$), methane, radon, hydrogen sulfide, total trihalomethanes, sulfur hexafluoride, nitrous oxide, sulfur dioxide, hydrogen, chlorine and/or bromine and the like. The systems are designed to resist clogging or fouling by suspended material in the liquids and are particularly useful in the measurement/monitoring of $CO_2$ in aqueous systems. The present disclosure also provides methods for rapidly determining the partial pressure of various gases including $CO_2$ ($pCO_2$) in a body of water. The systems and methods are particularly useful for measuring/monitoring $pCO_2$ in coastal waters and other bodies of water where $pCO_2$ can change rapidly and vary widely at sites that are in close proximity to each other. In addition to their use in coastal/environmental monitoring, the gas-liquid falling film equilibration system described herein can be used in industrial and laboratory settings where liquid-gas equilibration is needed. The equilibrators can be connected to a single or to multiple gas detectors (e.g., to measure multiple gas species simultaneously), including but not limited to analytical instruments such as gas chromatographs, mass spectrometers, instruments that perform absorption spectroscopy such as non-dispersive infrared gas analyzers, laser absorption spectroscopy, and cavity ring down spectroscopy, etc.

BACKGROUND

The measurement/monitoring of gases in various liquids is of both environmental and industrial importance. Various systems for the measurement of gases, including but not limited to $CO_2$, have been devised. Included in those systems are apparatus that assess the concentration of gases in the liquid directly (e.g., by spectral analysis or chemical reaction in the liquid phase) and those that force the gas from the solution by physical/chemical means (e.g., addition of acid, elevation of temperature, etc.) thereby permitting measurement in the gas phase.

Measurement of gases including greenhouse gases such as carbon dioxide ($CO_2$) and methane are of increasing importance as they have an effect on the regulation of the earth's temperature. It is estimated that roughly 30% of anthropogenic $CO_2$ leaves the atmosphere and enters the earth's oceans and other large bodies of water. These water bodies typically act as large sinks of $CO_2$, wherein dissolved $CO_2$ becomes carbonic acid, carbonate, and bicarbonate, with concomitant changes in pH. Unfortunately, devices for directly measuring pH in the natural environment are unreliable when deployed for any length of time, especially in systems with high productivity and/or sediment loads. In coastal systems, such as estuaries, where changes in salinity are common and biofouling extensive, measuring pH can be burdensome and inaccurate. Alternatively, measurements of changes in the partial pressure of $CO_2$ in the ocean can provide valuable and reliable information about changes in the acidity of the ocean. Nearshore coastal water pH measurements can also be made providing similar information.

Methods for measuring $pCO_2$ in oceans have mainly focused on measuring acidification in open ocean settings. These methods assume that acidification is driven by a stable air-sea $CO_2$ equilibrium, such that measurement of the ocean's $pCO_2$ is reflective of atmospheric $pCO_2$. The technology depends on large, expensive, and sparse autonomous buoys to characterize hundreds to thousands of $km^2$ of ocean surrounding them. Buoy data are supplemented by data from large, expensive, and sparse oceanographic research vessel taken during ocean transits.

Due to the complex make-up of nearshore coastal waters, an air-sea equilibrium rarely occurs and measurements must be made at higher frequency over space and time. Increased frequencies can assist to reliably characterize $pCO_2$ and pH. In nearshore waters the carbon cycle is much more complicated than in the open ocean, and land-sea interactions and ecosystem metabolism are frequently more acute drivers of $pCO_2$ than air-sea interactions. Nearshore waters are further complicated by biological activities such as photosynthesis and respiration and the $pCO_2$ of the water is far more dynamic than in the open ocean. Changes in $pCO_2$ are more rapid than in open ocean waters and $pCO_2$ can vary significantly over very short distances and time spans. Measurements must therefore be made much more frequently and much more densely in order to capture the natural temporal and spatial variability present.

Challenging environmental conditions also adversely affect the accurate measurement and long term monitoring of other gases that dissolve in water (e.g., radon, methane, etc.)

Accordingly, the development of measurement devices that are reliable enough to operate for significant periods of time without maintenance (e.g., resistant to clogging, freezing, and fouling) and which are capable of supporting suitably accurate assessments of gases in various liquids, including the waters of oceans, lakes, rivers, and streams, is useful for environmental, industrial, and residential purposes.

SUMMARY

The present disclosure describes an gas-liquid equilibration apparatus comprising:
  a chamber comprising an outer wall that is disposed substantially symmetrically about a central axis, the outer wall defining the interior surface of the chamber, the exterior surface of the chamber, and space within the chamber;
  an equilibration member within the chamber having an equilibration member surface, an axis of rotation, and a bisecting plane perpendicular to the axis of rotation positioned at the midpoint of the equilibration member's axis of rotation;
  the equilibration member being positioned within the chamber such that its axis of rotation and the central axis of the chamber coincide or substantially coincide;

the chamber, the exterior surface of the chamber, the interior chamber wall, the equilibration member within the chamber, and the space within the chamber being divided into an upper portion above the bisecting plane and a lower portion below the bisecting plane;

the space within the upper portion of the chamber being in liquid (fluid) and gas communication with the space within the lower portion of the chamber via one or more gaps between the equilibration member and the chamber wall;

at least one liquid inlet located in the upper portion of the chamber positioned such that a liquid introduced into the chamber from the one or more liquid inlet contacts the upper portion of the outer surface of the equilibration member;

at least one liquid outlet located in the lower portion of the chamber positioned to permit outflow of some or all of the liquid introduced into the chamber that collects in the lower portion of the chamber by gravity;

at least one gas inlet located in the wall of the lower portion of the chamber; and at least one gas outlet located in the wall of the upper portion of the chamber;

wherein at least a section of the upper portion of the chamber wall is removably-resealable to the remainder of the upper surface and/or the outer wall.

This disclosure also provides for methods of determining the amount of a gas (or gases) of interest present in a liquid using an apparatus as described herein comprising the following steps:

i) providing an apparatus;

ii) introducing the liquid into the chamber of the apparatus by way of the liquid inlet(s) such that it passes over the equilibration member thereby forming a film over all or part of the equilibration member's surface, and exits the apparatus by way of the liquid outlet(s);

iii) directing a carrier gas into the apparatus by way of the gas inlet(s) such that it flows over the equilibration member (the liquid film running down the surface of the equilibration member) in a direction that is counter current to the flow of the liquid and exits the chamber of the apparatus by way of the gas outlet(s);

iv) directing all or part of the gas that exits the chamber to at least one sensor of an analytical instrument that determines the amount of the gas (or gases) of interest present in the gas that exits the chamber.

Accordingly, the concentration of the gas of interest in the gas exiting the chamber can be used to determine the amount of a gas (or gases) of interest present in the liquid based on the output of the detection system.

Tests of the falling film liquid-gas equilibrators described herein across broad ranges of gas (e.g., $CO_2$) concentrations, liquid (e.g., water) and carrier gas (e.g., air) flow rates indicate that falling film equilibrators as described herein have the ability to produce consistent, precise, and accurate dissolved gas measurement (e.g., dissolved $pCO_2$ measurements) even across significantly different equilibrator dimensions.

The apparatus may be used to determine the concentration of a variety of gases in a diverse number of liquids, including the concentration of carbon dioxide in aqueous systems (e.g., fresh or salt water).

BRIEF DESCRIPTION OF THE DRAWINGS

FIG. 10A, fully assembled for operation; FIG. 10B, opened to show the equilibration member with the view from above; FIG. 10C, showing a rubber or plastic seal along the upper edge and an annular support within the chamber, the gas inlet is visible in the photo about 4'oclock on the chamber wall; FIG. 10D, the equilibrator with a 3.7-inch diameter equilibration member and a 0.565 liter chamber; FIG. 10E, side by side comparison of a 6-inch diameter equilibration member and a clear 4 liter chamber (left) and an 8-inch diameter equilibration member and a 7.57 liter chamber (right); FIG. 10F, side by side comparison of a 3.7-in diameter equilibration member in clear 1 liter chamber (left) and an 8-inch diameter equilibration member and 7.57 liter chamber (right).

DETAILED DESCRIPTION

Definitions

An equilibrator is an apparatus for contacting a gas and a liquid so as to exchange one or more gases between the phases. The term equilibrator does not mean the apparatus brings the two phases (gas and liquid) necessarily into perfect equilibrium, but rather brings the phases to a state approaching equilibrium or a dynamic equilibrium so that the amount and/or relative changes in the amount of gases/volatile materials in the liquid can be determined.

A liquid inlet is a point in the surface of the chamber wall where liquid enters the chamber. The liquid inlet may terminate at or be in the form of a nozzle.

A nozzle is an extension or projection at the gas inlet or liquid inlet that directs the flow of gas or liquid within the chamber. Liquid inlets have an opening with a minimum inner diameter to avoid plugging and promote complete wetting of the equilibrium member, thereby optimizing the generation of a falling film gas exchange surface.

"Amount" of a gas or gases as used herein may be expressed by any suitable measure including concentration in the form of molarity, weight per volume (e.g., volume of carrier gas), volume/volume (e.g., per volume of carrier gas, or percent volume of carrier gas), partial weight or mass (grams gas of interest/gram of gas or liquid, such as ppm by weight), part per million by volume (ppmv), or partial pressure.

Calibration gas or calibrator gas is a gas having a known amount of the gas of interest.

Carrier gas as used herein is a gas, other than the gas of interest, that is passed through the equilibrator and into which the gas of interest diffuses, and which may be subject to analysis to determine the amount of the gas of interest present.

The term, "removably-resealable," as used herein means capable of being removed from a location on an object (e.g., the equilibrator chamber wall) and replaced in that location to form a seal. More specifically, with regard to a section of the chamber wall, removably-resealable means that a section of the chamber wall can be removed to provide access to the interior of the chamber and then replaced and sealed sufficiently to the remainder of the chamber wall to permit operation of the apparatus (e.g., without loss of carrier gas or liquid from the chamber that would interfere with its operation).

Ellipsoidal as used herein means having the form of an ellipsoid.

Ovoidal as used herein means having the form of an ovoid (e.g., egg shaped).

Spheroidal as used herein means having the form of a sphere or spheroid.

Figure 5A:
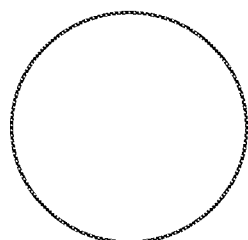
FIGS. 5A-5N show generalized cross sections of equilibration members including 5A spherical, 5B ellipsoidal, 5C ovoidal, 5D fusiform shape, 5E hemisphere, 5F hemiellipsoid, 5G hemiovoid, 5H domed frustum (domed frustoconical section), 5I domed vertical right column, 5J column having oscillating sides (e.g., sinusoidal changes in the column radius), 5K cone having sinusoidal oscillating sides (column with sinusoidal changes in the column radius), 5L a series of spheroids or discs, 5M four spheroids, and 5N a series of spheroids or disc of increasing size.
Figure 5B:
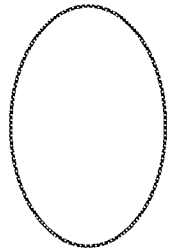
Figure 5C:
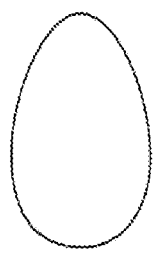
Figure 5D:
Figure 5E:
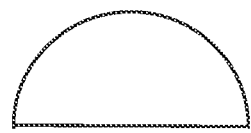
Figure 5F:
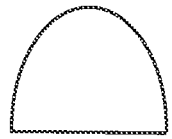
Figure 5G:
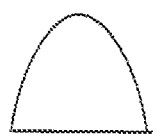
Figure 5H:
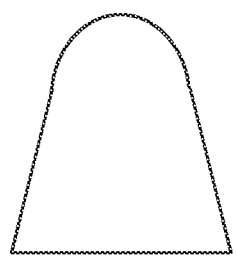
Figure 5I:
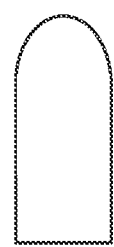
Figure 5J:
Figure 5K:
Figure 5L:
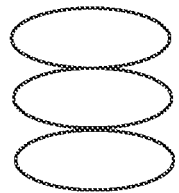
Figure 5M:
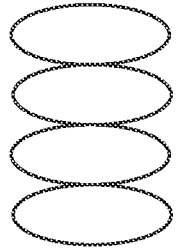
Figure 5N:
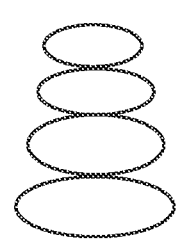

Vertically stacked equilibration member(s) means equilibration members formed from a series of element having an axis of rotation that when aligned vertically in the equilibration chamber each have their axis of rotation substantially aligned with the central axis of the equilibration apparatus. See. e.g., FIGS. 5A through 5N.

Description

The measurement of $CO_2$ and other gases or volatile materials present in liquid (e.g., aqueous) samples may be conducted using a variety of techniques. In many techniques the gas(es) of interest are removed/forced out of the liquid for measurement in the gas phase. The gas phase may include a carrier gas or mixture of carrier gases into which the gas(es) of interest in the liquid move (e.g., exchange or are added to the carrier gas(es)). The movement of gases out of the liquid may be accomplished by a number of processes including, but not limited to, alteration of the chemical composition of the liquid (e.g., acidification), reduction of the pressure, and passive diffusion. A variety of different equilibration apparatus or "equilibrators" has been developed with the goal of efficiently exchanging/equilibrating the gases in the liquid phase with a carrier gas that is in turn directed to the sensor of a detection/analysis instrument (gas analyzer) for measurement of the gases of interest. Among the equilibrator designs are the "shower type", "bubble Weiss type", and "laminary flow type" described by Frankignoulle et al. (Water Res. Vol. 35, No. 5, pp. 1344-1347, (2001)). While each of such systems may be useful, they suffer from a variety of disadvantages including, but not limited to, the inability to handle materials with suspended particles, susceptibility to fouling (e.g., biofouling), difficulty in removal of deposits (cleaning) built up by suspended particles and/or fouling, and instability when subject to tipping or motion during measurement.

The present disclosure describes, and provides for the use of, a falling film type of equilibrator that provides a rapid response time that is governed by the dead time (i.e. time after a change to the input before its initial detection) and the lag time (i.e. how fast the equilibration/detection process proceeds), the specific values of which depend on the specifics of the equilibrator design and the detection instrument that is being used. The time constant tau ($\tau$), also known as the e-folding time, is the time necessary for an instrument to respond to an induced step change. $\tau = 1/e$ decay in concentration (n $\tau$=time at which $C_t/C_0 = 1/e^{dn}$; e.g., 3 $\tau$=time when $C_t/C_0 = 1/e^3$) when step change is from high to low. Conversely, when the step change is from low to high concentrations, the response is given by n $\tau$=time when $C_t/C_0 = 1 - 1/e^n$. For spherical falling film equilibrators described herein (e.g., with equilibration member diameters of around 3.5 to 10-inch diameters), $\tau$ ~3 minutes and 3 $\tau$ (i.e. to reach 95% response) ~8 minutes for small diameter equilibrators for carbon dioxide steps from about 100 ppmv to about 50,000 ppmv. For an equilibrator having a VRC chamber with a volume of about 7.57 liters and a spherical equilibration member about 8 inches (20 cm) in diameter operated at a water flow rate in the range of 225-380 liters per hour and a one (1) liter/minute carrier gas (air) flow rate, τ can be as low as about 3 to 4 minutes, although it may be longer (e.g., about 4 to about 6 minutes, about 6 to about 8 minutes, or about 8 to about 9 minutes) depending on the particular operating conditions. The dead time (time from the initiation of the step change in dissolved gas until the detectors first respond) for such an equilibrator operated under the same conditions is generally less than about 1 minute. For equilibrators where the head space has been minimized, the response time for carbon dioxide measurements may be less than 3 minutes (e.g., less than 2.5, 2.0, 1.5 or 1.0 minutes, or in a range from 1.0-3.0 minutes, 1.0-2.0 minutes, or 2-3 minutes). Similarly, dead times can be less than one (1) minute (e.g., less than 50 seconds, 40 second, 30 seconds, or 20 seconds, or in a range from 20 seconds to 1 minute, 20-40 seconds, or 40 seconds to 1 minute).

In a first embodiment the equilibrator comprises a chamber formed of a wall w having a liquid inlet 1 and liquid outlet 2 subject to measurement; an equilibration member em enclosed within the chamber; and a gas inlet 3 and gas outlet 4 for a carrier gas such that the carrier gas flows substantially counter current to the flow of liquid through the chamber. The equilibration member has a surface over which the liquid can form a film over all or part of the surface area (e.g., over greater than 50, 60, 70, 80, 90, or 95% of its surface area) where flow is not inhibited or impeded by the shape or the design or equilibrator orientation). In such an embodiment the equilibration member may be wettable by the liquid (e.g., the equilibration member is hydrophilic and the liquid is aqueous). In embodiments, the equilibration member is hydrophilic and the contact angle of the equilibration member with water is less than about 90°, less than about 80°, less than about 70°, less than about 60°, less than about 50°, less than about 40°, less than about 30°, less than about 20°, or less than about 10°, as measured by a goniometer at 22° C.

In an aspect of the first embodiment (second embodiment) the equilibrator comprises:

a chamber comprising an outer wall that is disposed substantially symmetrically about a central axis, the outer wall defining an interior surface of the chamber, an exterior surface of the chamber, and space within the chamber;

an equilibration member within the chamber having an equilibration member surface, an axis of rotation, and a projected bisecting plane bp that is perpendicular to the axis of rotation, the bp positioned at the midpoint of the equilibration member's axis of rotation (e.g., where the em is a sphere the bp would pass through its equator);

the equilibration member being positioned within the chamber such that its axis of rotation and the central axis of the chamber coincide or substantially coincide (e.g., substantially align);

the chamber, the interior and exterior surface of the chamber, the chamber wall, the equilibration member within the chamber, and the space within the chamber being divided into an upper portion above the position of the bisecting plane and a lower portion below the bisecting plane;

the space within the upper portion of the chamber being in liquid and gas communication with the space within the lower portion of the chamber via one or more gaps between the equilibration member and the chamber wall;

a liquid inlet located in the upper portion of the chamber positioned such that a liquid introduced into the chamber from the liquid inlet contacts the portion of the equilibration member located in the upper portion of the chamber;

a liquid outlet located in the lower portion of the chamber positioned to permit outflow of some or all of the liquid and suspended solids (e.g., sediments, detritus, phytoplankton, etc.) introduced into the chamber that tend to collects in the lower portion of the chamber by gravity;

a gas inlet located in the wall of the lower portion of the chamber; and a gas outlet located in the wall of the upper portion of the chamber.

During operation the liquid (e.g., water) draining out of the outlet forms a seal such that gas may not enter or exit the chamber. Importantly, this seal will self-correct internal pressure to match ambient atmospheric pressure (i.e. if either positive or negative pressures begin to the develop inside the equilibrator chamber, the seal will be momentarily broken, allowing inside and outside pressure to equalize, with little or no effect on carrier gas-liquid (e.g., air-water) equilibration. In such an embodiment, at least a section of the upper portion of the chamber wall may be removably-resealable to the upper portion of the exterior surface of the chamber and/or the upper portion of the chamber wall.

In an aspect of the first embodiment (a third embodiment) the equilibrator comprises:

a chamber comprising an outer wall that is disposed substantially symmetrically about a central axis, an upper surface, and a lower surface, that together define an interior surface of the chamber, an exterior surface of the chamber, and space within the chamber;

an equilibration member within the chamber having an equilibration member surface, an axis of rotation, and a bisecting plane perpendicular to the axis of rotation (e.g., an equilibration member substantially spheroidal, ellipsoidal, ovoidal, or other shape discussed below, see also FIGS. 5A-5N and 6A-6N), with the bisecting plane positioned perpendicular to the axis of rotation at the midpoint of the equilibration member's axis of rotation;

the equilibration member being positioned within the chamber such that its axis of rotation and the central axis of the chamber coincide or substantially coincide such that the bisecting plane of the equilibration member is substantially perpendicular to the central axis of the chamber;

the chamber, the exterior surface of the chamber, the chamber wall, the equilibration member within the chamber, and the space within the chamber being divided into an upper portion above the position of the bisecting plane and a lower portion below the bisecting plane;

a liquid inlet located in the upper portion of the chamber positioned such that a liquid introduced into the chamber from the liquid inlet contacts the portion of the equilibration member located in the upper portion of the chamber;

a liquid outlet located in the lower portion of the chamber positioned to permit outflow of some or all of the liquid introduced into the chamber that collects in the lower portion of the chamber by gravity;

a gas inlet located in the lower portion of the chamber; and a gas outlet located in the upper portion of the chamber; wherein at least a section of the upper portion of the chamber is removably-resealable to the remainder of the upper surface and/or the outer wall.

In such an embodiment, at least a section of the upper portion of the chamber wall may be removably-resealable to the upper portion of the exterior surface of the chamber and/or the upper portion of the chamber wall.

Figure 3:
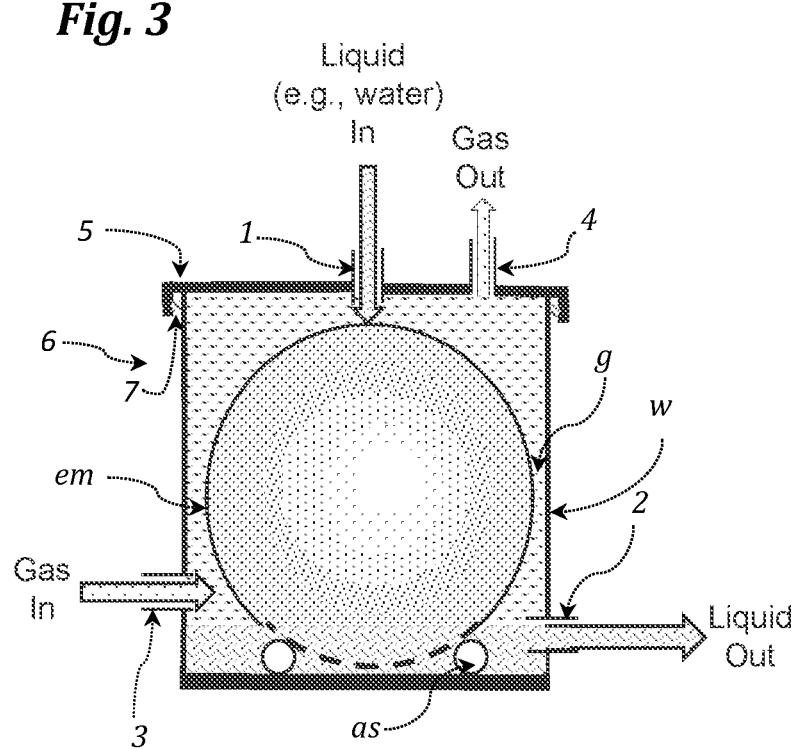
FIG. 3 shows a schematic cutaway of an equilibrator with a substantially cylindrical chamber and a spherical equilibration member as in FIG. 2. As diagramed, the planar upper surface of the cylinder 5 has a lip 6 and is removably-resealable to (against) the cylindrical wall, at location 7 (via e.g., an o-ring). In such an embodiment, the planar upper surface acts like a substantially air-tight/water-tight "lid" on the cylindrical chamber. The annular support as supporting the equilibration member is shown below the level of liquid (e.g., water) in the chamber.
Figure 4:
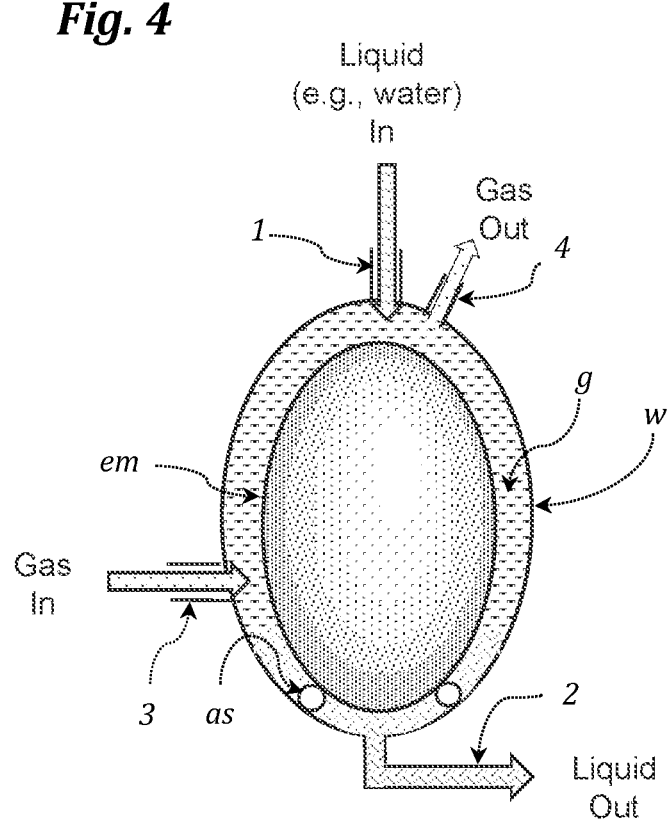
FIG. 4 shows a schematic cutaway of an equilibrator with a substantially ellipsoidal chamber and an ellipsoidal equilibration member. Holes, gaps, or channel in the annular support as permit liquid introduced through inlet 1 to reach the liquid outlet 2.

In any of the first, second or third embodiments recited above, the chamber may be a vertical right cylinder. In some embodiments, the section of the upper portion of the chamber wall that is removably-resealable to the upper portion of the exterior surface of the chamber, and/or the upper portion of the chamber wall, may be the planar upper surface of the cylinder 5 or a portion thereof. In such an embodiment, the planar upper surface may have a lip 6, which seals against the chamber wall at, for example, location 7, so that it acts like a "lid" on the cylinder of the chamber. The seal at location 7 in FIG. 3 is shown as an o-ring; however, other types of seals may be employed alone or in addition to o-rings, including compression seals and snap fit lids. See, e.g., FIG. 3. The liquid inlet 1 and/or gas outlet 4 may be positioned in the planar upper surface, and either or both may be positioned in a portion of the planar upper surface that is removably-resealable to the remainder of the chamber.

In other embodiments, including the first, second or third embodiments recited above, the chamber is not a vertical right cylinder. In such embodiments, the chamber may be a shape, such as an ovoid, ellipsoid, or spheroid, that more closely conforms to the shape of the equilibration member leaving a lower headspace volume that will shorten the overall response time of the equilibrator to changes in the gas content of the liquid introduced for sampling.

Various features and components of the equilibrators described herein are discussed in further detail below (e.g., the shape of the equilibration member and/or chamber, material for constructing the equilibrator, and placement of inlets and outlets).

The use of the falling film equilibrators having the above-mentioned designs, which are further described herein, and particularly those with spheroidal, ellipsoidal and ovoidal equilibration members offers a variety of advantages. Such equilibrators offer the ability to form and sustain a reliable and effective thin layer falling film. Because the design uses an equilibration member centrally located in the chamber, the orientation and/or disturbance of the equilibrator (e.g., placement on a non-level surface or movement on a boat or floating platform) is far less critical to its successful operation than falling films generated on other surface geometries such as vertical tubes or planar surfaces). This is especially true for embodiments where the equilibration member has a spheroidal, ovoidal, or ellipsoidal surface for falling film generation. This contrasts with vertical falling films used, for example, in industrial applications such as falling film evaporators that contain hundreds of individual vertical tubes that can be several stories tall. These systems are stationary as they need to remain plumb to the ground for effective use as they are prone to suboptimal flow or failure if disturbed or deviated from a vertical position. In addition, vertical tube equilibrators must be engineered and built to higher tolerances than the equilibrators described herein. Furthermore, the mechanism for introducing liquid at the tops of vertical tube-type equilibrators must be properly designed, and the flow carefully controlled, if sustained falling films are to be maintained.

In contrast, given adequate water flow rate, the falling film design described herein has the advantage of maintaining a sustainably wetted surface for gas exchange (e.g., fully wetted or greater than 50%, 60%, 70%, 80%, 90%, or 95% wetted), even when the water intake is tilted up to nearly 45° from vertical. Thus, physical disturbances and non-plumb placements do not affect the generation and maintenance of falling films and, by extension, do not disturb the proper function of the air-water equilibrator.

The equilibrators described and provided for herein (e.g., those with spherical, ellipsoidal, or ovoidal equilibration members) also offer some distinct advantages over shower, so-called marble laminary flow, bubbling, and membrane equilibrator designs. Each of those designs has narrow passages that are prone to clogging (blockage) and/or fouling (buildup of deposits). Clogging and fouling may have a variety of sources including sediments, suspended particles, deposition of minerals from the liquid, phytoplankton, detritus, biofouling by marine and/or aquatic organisms (e.g., barnacles, bryozoans, hydroids, etc.), and combinations of any two, three or more thereof.

Clogging and/or fouling can easily compromise water flow and operation of air-water equilibrators. For example, equilibrator designs that employ a showerhead to create water droplets/mists will cease to function with even minor clogging/fouling, as will equilibrators that employ air stones or frits (which foul from materials in the liquid) that are used to introduce carrier gases into bubbling equilibrators. Likewise, sediments and phytoplankton can clog the interstices among marbles in vertical laminary flow equilibrators, thereby compromising gas exchange. Trapped organic material and organisms can also promote biogenic processes that affect gas concentrations inside the equilibrator (e.g., respiration and photosynthesis). Clogging and biofouling greatly reduce the utility of these equilibrator designs, particularly where eutrophic and/or turbid aqueous samples are being analyzed. This includes eutrophic and/or turbid samples of water from coastal oceans, estuaries, lagoons, rivers, streams, lakes, reservoirs, and the like.

The falling film equilibrators described and provided for herein (e.g., those with spheroidal, ellipsoidal, and ovoidal equilibration members) use relatively large and difficult to clog water ports that provide unimpeded free flowing liquid (e.g., water) to form the falling film. As such, they avoid narrow channels or paths for liquid flow that are prone to blockage by clogging and fouling. In some embodiments, anti-fouling coatings (e.g., marine anti-fouling paint with, for example, copper incorporated) can be used on the surface of the equilibrator. In addition, the internal walls of the equilibrator chamber and fittings can be coated with anti-fouling treatments, coatings or paints to further prevent biofouling. In an embodiment at least the inner surface of the chamber is coated with a hydrophobic coating, or hydrophobic and oleophobic coating, that resists fouling. In addition, the nature of the liquid flow through the chamber tends to sweep/carry particulate matter off the equilibration surface and out of the chamber, preventing buildup.

In addition to being resistant to clogging and fouling, the spherical falling film equilibrators described and provided for herein (e.g., those with spheroidal, ellipsoidal, and ovoidal equilibration members) are comprised of a very few parts that may be made of durable materials that can withstand impact (e.g., durable plastics, or stainless steel). In embodiments described herein, the equilibrator comprises a section of the chamber that is easily removed, thereby opening the chamber and permitting the apparatus to be quickly cleaned by hand in the field. In an embodiment the section of the chamber wall that is removable is of sufficient size to permit the equilibration member to be removed. The removable section of the chamber wall is designed to be placed back in position and sealed to the remainder of the chamber (a removably-resealable section).

As the equilibrators described and provided for herein do not rely on small orifices, channels, or interstices for gas exchange and proper function, the cleaning and maintenance of the equilibrators are minimized and can be performed far less frequently than for the traditional air-water equilibrators described above. As such, the equilibrator design can be deployed in the field for much longer periods of time between maintenance checks.

1. Equilibration Members

The equilibration member, which is disposed inside of the chamber of the equilibration apparatus, provides a surface upon which the liquid subject to measurement (e.g., water or salt water) forms a film as it passes over the surface and is drawn downward by gravity. The equilibration apparatus described herein may employ equilibration members in a variety of shapes and sizes. The equilibration members are generally symmetrical about a central axis, which extends from the top to the bottom of the equilibration member, and as indicated below is used to center the member within the chamber. As a matter of locating, among other things, liquid inlet(s), liquid outlet(s), gas inlet(s) and gas outlet(s), the equilibration member may be understood to be divided into an upper portion and a lower portion by a bisecting plane that is projected substantially perpendicular to the central axis at the midpoint between the top and bottom of the equilibration member.

Figure 6A:
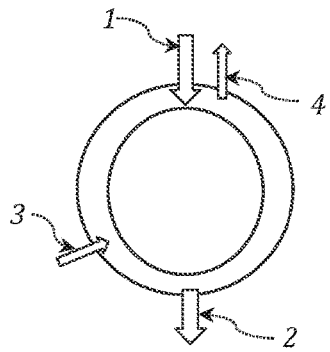
FIGS. 6A-6N show generalized cross sections of equilibrators incorporating the equilibration members shown in FIG. 5. Each equilibrium member is shown in an equilibrium chamber having a liquid inlet 1, a liquid outlet 2 a gas inlet 3, and a gas outlet 4 indicted by arrows.
Figure 6B:
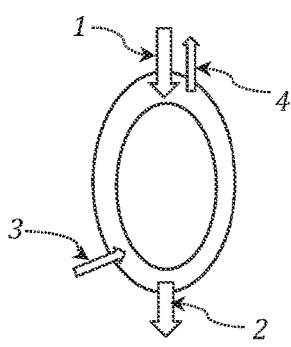
Figure 6C:
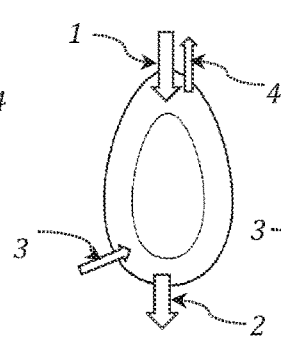
Figure 6D:
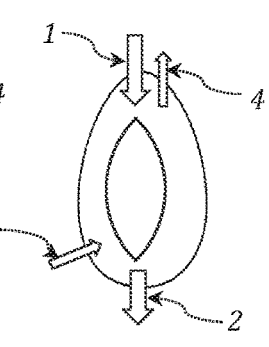
Figure 6E:
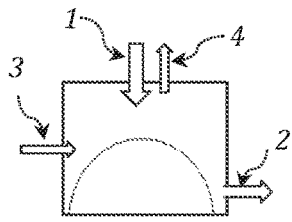
Figure 6F:
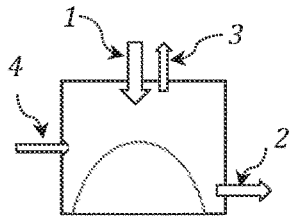
Figure 6G:
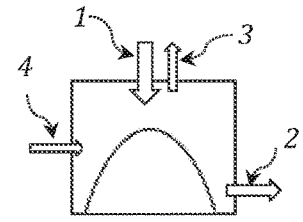
Figure 6H:
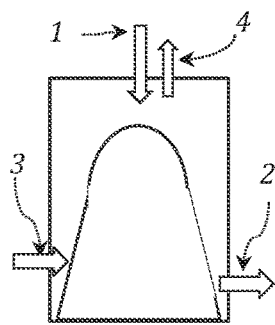
Figure 6I:
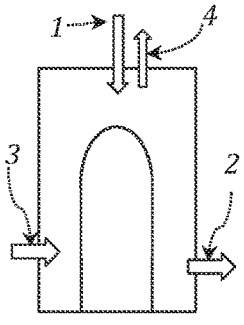
Figure 6J:
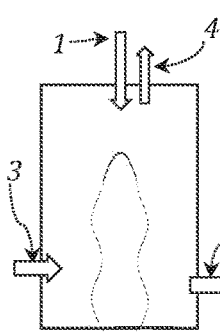
Figure 6K:
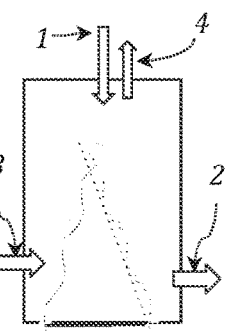
Figure 6L:
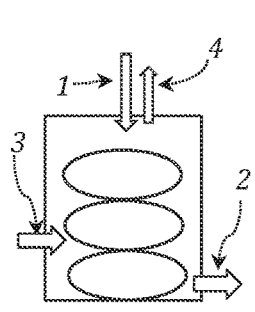
Figure 6M:
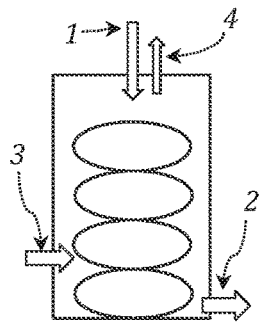
Figure 6N:
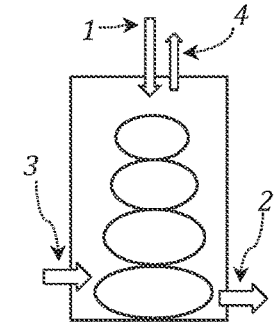

In various embodiments the shape of the equilibration member is substantially a spheroid, an ellipsoid, an ovoid, a fusiform shape, a hemisphere, a hemiellipsoid, a hemiovoid, a domed frustum, a domed column, a column having oscillating sides (e.g., sinusoidal changes in the column radius), a cone having sinusoidal oscillating sides (sinusoidal changes in the column radius), or a series of spheres or discs (two, three, four or more) aligned along a central axis. See FIGS. 5A-5N. Any of the foregoing may have one, two, three, four or more spiral grooves along the surface to increase the surface area of the equilibration member.

Where the equilibration member is in the form of a hemisphere, a hemiellipsoid, a hemiovoid, or a domed frustum, the equilibration member may be formed against or as part of the lower portion of the chamber See, e.g., FIGS. 6E-6G.

In one embodiment the equilibration member is substantially spheroidal, ellipsoidal or ovoidal. In such an embodiment the equilibration member may be a sphere, ellipsoid, or ovoid.

In an embodiment the equilibration member is substantially spheroidal.

In an embodiment the equilibration member is substantially ellipsoidal.

In an embodiment the equilibration member is substantially ovoidal.

The equilibration member may occupy a volume that is greater than 50%, 60%, 70%, 75%, 80%, 85%, 90%, or 95% of the interior volume of the chamber (e.g., from 50% to 70%, from 60% to 80%, from 70% to 90%, from 80% to 95%, or from 90% to 95%). In an embodiment, where the chamber is substantially a virtual right cylinder (VRC), the equilibration member may occupy greater than about 50%, 60%, 70%, 75%, 80%, 85%, 90%, or 95% of the interior volume of the chamber. In another embodiment, where the chamber is substantially a VRC, and the equilibration member is spheroidal, the volume of the equilibration member is less than about 70% of the interior volume of the chamber (e.g., less than 65%, 60%, 50%, 40% or 30% of the interior volume of the equilibration chamber).

As discussed above, the equilibration member may have a surface over which the liquid can form a continuous film over all of its surface area, or the liquid can form a continuous film over greater than 50%, 60%, 70%, 80%, 90% or 95% of its surface area (e.g., flow is not impeded by the shape of the design). In such an embodiment the equilibration member may be wettable by the liquid. In an embodiment, where the liquid subject to measurement is an aqueous liquid, the equilibration member is hydrophilic. In such an embodiment, the contact angle of the equilibration member with water can be less than 90°, 80°, 70°, 60°, 50°, 40°, 30°, 20°, or 10° measured by a goniometer at 22° C.

The equilibration members themselves may be made from a variety of materials and may be, for example, hollow, solid or made of a shell filled with another material. Where a shell type structure is used, the equilibration members may be filled with a foam or foam-like material (e.g., a polyurethane foam) having a closed or open cell structure. Where equilibration members are hollow, they are designed to be totally sealed, or sealed sufficiently that only an insubstantial amount of gas or liquid can enter the member's interior space(s). For example, a hollow equilibration member may have a small hole (e.g., pin hole) to prevent pressure differences with the gas and/or liquid within the chamber.

2. Chambers

The chamber of the equilibration apparatus can serve a variety of purposes including positioning and supporting the equilibration member and the gas and liquid inlets and outlets. The chamber may have any suitable shape provided it does not interfere with the passage of gas through the chamber or the formation or movement of the falling film of liquid introduced into the chamber as it is drawn downward by gravity over the surface of the equilibration member. The chamber comprises an outer wall having a thickness t, with the wall defining the interior surface of the chamber, the exterior surface of the chamber, and space within the chamber. In various embodiments the chamber wall is disposed substantially symmetrically about a central axis and may have a cylindrical, spheroidal, ellipsoidal or ovoidal shape. Where the chamber is spheroidal, it may be a sphere, or it may have a prolate or oblate spherical shape. Regardless of exact shape of the chamber, for minimization of response dead time and rapidity of the response time headspace will be closer to optimization when the chamber's interior surface is substantially parallel to, or substantially follows the contour of, the equilibration member's outer surface.

As discussed above, although the chamber may have a variety of shapes, where the chamber substantially conforms to the shape of the equilibration member, the headspace (volume) within the chamber surrounding the equilibration member and the film of falling liquid is minimized. Minimizing the space within the chamber around the equilibration member permits the equilibrator to more rapidly respond to changes in the gas content of the liquid in the falling film. The improved response time is a function of, among other things, the more rapid turnover of the gas within the chamber at any given carrier gas flow rate and the smaller volume of gas into which the incoming carrier gas will be mixed with/displace. The response time can also be improved by limiting areas within the chamber that may form eddies or interfere with the laminar flow of carrier gas from the gas inlet to the gas outlet. Accordingly, in embodiments, both the equilibration member and the chamber may have a shape that is spheroidal, ellipsoidal, or ovoidal.

In an embodiment, the chamber is in the form of a VRC. Where the chamber has the overall shape of a VRC, the equilibration member housed within it may be of any shape discussed above including spheroidal. Where the chamber is in the form of a VRC, and it is desirable to minimize the space around the equilibration member, the equilibration member may have an ellipsoidal, an ovoidal, or a prolate or oblate spheroidal shape.

Regardless of its shape, the chamber, the exterior surface of the chamber, the chamber wall, the equilibration member within the chamber, and the space within the chamber may be conceptually divided into an upper portion and a lower portion. The upper portion is defined as the section above the level of the equilibration member's bisecting plane and the lower portion as the section below that bisecting plane when the equilibration member is located within the chamber in position for the apparatus to operate such that its axis of rotation and the central axis of the chamber coincide or substantially coincide.

The chamber may be formed with a chamber wall section that is removably-resealable to permit access to the interior of the chamber. The section may be of sufficient size to permit access for monitoring, cleaning and maintenance, or even removal of the equilibration member for inspection, cleaning and/or replacement. The seal may be any suitable type, including those formed by o-rings, gaskets, snap-fit, compression or frustoconical sections (e.g., with a seat and threaded sections), or combinations of any thereof. The section of the chamber wall that is removably-resealable may be located in the lower portion of the chamber. Alternatively, the section that is removably-resealable may be located in the upper portion of the chamber. Where the chamber is in the form of a VRC, or substantially in the form of a VRC, the removably-resealable section may constitute all or part of the planar upper surface of the cylinder. In an embodiment, the removably-resealable section comprises the upper planar surface of the VRC and a seal at or proximate to its circumference that engages all or part of the cylindrical wall of the cylinder. In such an embodiment the vertical wall of the VRC may comprise one or more ridges to retain the removably-sealable upper section and/or a seal or a sealing surface that engages the upper portion.

The interior volume of a chamber may be varied over a substantial range, for example from about 1 to about 25 liters (e.g., from about 1 to about 4, from about 1 to about 8, from about 9 to about 16, from about 12 to about 25, from about 16 to about 20, from about 18 to about 25, or from about 20 to about 25).

Using a chamber that has a shape that substantially matches the contoured shape of the equilibration member, the head space can be reduced. For example a spheroidal chamber and spheroidal equilibration member combination can have chamber volume: equilibration volume ratio from about 3.3 to 2.0 with a equilibration member to head space ratio from about 0.3 to 1.0 (head space volume divided by equilibration member volume).

3. Positioning of the Equilibration Member and the Location of the Inlets and Outlets The equilibration member may be positioned and held in place within the chamber in a number of different ways, including those that are permanent (affixing the equilibration member to the interior of the chamber in a non-removable manner), non-permanent (holding the equilibration member in place by contact with the chamber interior or supports within the chamber interior (e.g., annular supports, pedestals, etc.).

Examples of permanent ways of affixing the equilibration member to the interior of the chamber include the use of adhesives or fusing the equilibration member to the chamber at one or more points.

Non-permanent methods of positioning and holding the equilibration member in place permit the removal of the equilibration member from the chamber for cleaning and/or servicing the apparatus.

In an embodiment the equilibration member is held in place in a non-permanent manner by gravity and is directly removable from the chamber once all or part of a section of the chamber wall that is sufficient in size to extract the equilibration member is removed. Among the non-permanent structures that may be used to retain the equilibration member in place are studs and/or rings on the interior surface of the chamber that position and hold the equilibration member in place during operation by contacting it. Alternatively, studs and/or rings may be on the surface of the equilibration member and hold the member in place by contacting the interior surface of the chamber. Another alternative is the use of a combination of studs and/or rings attached to the chamber and equilibration member. The use of non-permanent methods of positioning the equilibration member permits the equilibration member to be removed (e.g., lifted) out of the camber for cleaning and maintenance of the member and/or chamber once a removably-resealable chamber wall section is disengaged and the chamber is opened.

The equilibration member may also be affixed to the chamber using non-permanent connections such as screws,

| VRC chamber and Spheroidal Equilibrator Combination | Chamber Diameter (cm) | Approximate Chamber Volume (cm$^3$) | Equilibration Member Diameter (cm) | Approximate Equilibration Member Volume (cm$^3$) | Approximate Ratio of the Chamber Volume to Equilibration Member Volume |
|---|---|---|---|---|---|
| #1 | 11-12 | 950-1360 | 10 | 524 | 1.8-2.9 |
| #2 | 13-14 | 1600-2440 | 12 | 904 | 1.8-2.9 |
| #3 | 15-16 | 2600-3900 | 14 | 1437 | 1.8-2.9 |
| #4 | 17-18 | 3900-5800 | 16 | 2145 | 1.8-2.9 |
| #5 | 19-20 | 5500-8250 | 18 | 3053 | 1.8-2.9 |
| #6 | 21-22 | 7500-11300 | 20 | 4189 | 1.8-2.9 |
| #7 | 23-24 | 10000-15000 | 22 | 5575 | 1.8-2.9 |
| #8 | 25-26 | 13000-19550 | 24 | 7238 | 1.8-2.9 |
| #9 | 27-28 | 16550-24850 | 26 | 9202 | 1.8-2.9 |
| #10 | 29-30 | 21500-31000 | 28 | 11494 | 1.8-2.9 |
| #11 | 31-32 | 25450-38200 | 30 | 14137 | 1.8-2.9 |
| #12 | 33-34 | 30900-46300 | 32 | 17157 | 1.8-2.9 | clamps, latches, magnets and the like that can be removed or uncoupled to free the equilibration member and permit its removal from the chamber once a removably-resealable chamber wall section is disengaged and the chamber is opened.

In an embodiment, a cylindrical pedestal is placed vertically beneath the equilibrium member with the axis of rotation the cylindrical member, the equilibration member, and the central axis of equilibration chamber all substantially aligned. The pedestal, which may be permanently or non-permanently affixed to the equilibration member, positions the equilibration member properly for generation of falling liquid film and also serves as an additional falling film surface as liquid transitions from the equilibrium member and flows over the pedestal surface before draining out of container. Where the pedestal is solid, or does not readily permit gas to exchange with any space within the pedestal, then volume of the pedestal positioning member also reduces the amount of headspace volume inside the equilibrium chamber.

In an embodiment, the equilibration member is positioned within the chamber by a ring, annular projection, or concave section formed in the lower portion of the chamber. In such an embodiment, the equilibration member may be made of a magnetically susceptible material or comprise a magnet or magnetically susceptible material, such that the equilibration member may be magnetically engaged to the interior surface of the chamber by a magnet located (positioned) on or in the chamber wall. The equilibration member may also be magnetically engaged in a position proximate to, but not in direct contact with, the chamber wall (e.g., the lower portion of the chamber wall) where it is supported by studs or an annular element (ring). Such an embodiment is shown in FIG. 3, where the chamber is a VRC and a spherical equilibration member is held against an annular element that is in contact with the substantially planar lower interior surface of the VRC.

In an embodiment the equilibration member is mounted inside a chamber using a series of stand-off posts alone or in combination with an annular element.

In an embodiment the equilibration member is positioned inside the equilibration chamber by floating on a surface of the liquid (e.g., water) that accumulates at the bottom of the equilibration chamber prior to draining. In this embodiment, a spherical equilibrium member can either rotate freely or remain relatively stationary depending on the attack angle and force of the water introduced into the chamber and onto the member through in inlet port (e.g., the liquid in the chamber acts as a hydrodynamic bearing). In such an embodiment, the equilibration member can be kept approximately centered in the chamber by the use of small posts or ribs (e.g., either parallel to or perpendicular to the central axis) on the chamber's inside surface.

In an embodiment, the equilibration member may be suspended from the upper portion of the chamber. In one such embodiment, the equilibration member is suspended by a flexible material (e.g., a strand of wire, string, plastic, fiber glass, rubber etc.) from the upper portion of the chamber at or near the point where the central axis passes through the chamber wall (e.g., at or near the center of the lid). Equilibration members suspended from the upper portion of the chamber can act like a pendulum and have the tendency to stay centered under the liquid entering the chamber from a centrally located liquid inlet when the chamber is tilted.

Equilibration members are generally positioned in the chamber such that there is a gap between the equilibration member and the chamber wall. The gap permits a liquid (e.g., water) introduced into the upper part of the chamber that runs over the equilibration member to reach the lower portion of the chamber unimpeded. At the same time, air or a carrier gas introduced into the lower part of the chamber via the gas inlet can freely move to the upper portion of the chamber through the gap. The gap is generally distributed uniformly around the equilibration member but there does not have to be a completely uniform gap and the equilibration member may even contact the chamber wall at one or more points. While the size of the gap between the chamber wall and the equilibration member may vary, a gap in the range of 0.1 cm to 2.5 cm (0.1-0.5, 0.5-1.0, 1.0-1.5, 1.0-2.0, 1.5-2.5, or 2.0-2.5) will generally be sufficient to permit passage of the gas and the liquid.

In an embodiment, the chamber is a VRC having an interior volume of from about 1.6 liters to 25 liters and a diameter of about 6.5 cm to about 33 cm. In such an embodiment, a spherical equilibration member having a diameter that is from about 0.2 cm to about 5 cm (e.g., about 0.2 cm-about 1.0 cm, about 0.2 cm-about 2.0 cm, about 2.0 cm-about 4.0 cm, or about 2.5 cm-about 5 cm) less than the inner diameter of the chamber may be employed. Accordingly, where there is a difference in diameter of 0.2 cm to 5 cm and the equilibration member's axis of rotation and the central axis of the chamber are aligned, there will be a uniform gap of from about 0.1 cm to about 2.5 cm (e.g., about 0.1 to about 0.5 cm, about 0.5 to about 1.0 cm, about 1.0 to about 2.0, or about 2.0 to about 2.5 cm) between the equilibration member and the chamber wall at the equator of the equilibration member or the location of the equilibration member with the greatest diameter or radius.

In another embodiment, the chamber is spherical and has a volume of from about 1.0-18.0 liters (12.7 cm to about 33.0 cm in diameter), and the equilibration member is spherical and has a diameter that is less than the inner diameter of the chamber's interior by about 0.2 cm to about 8 cm. Accordingly, when the equilibration member's axis of rotation and the central axis of the chamber are aligned, there will be a uniform gap of from about 0.1 cm to about 4 cm (e.g., about 0.5-about 1.0 cm, about 1.0-about 2.0, or about 2.0-about 4 cm) between the equilibration member and the chamber wall.

The liquid inlet(s) may be positioned in the upper portion of the chamber such that liquid introduced via the liquid inlet(s) can form a film over greater than 50%, 60%, 70%, 80%, 90%, or 95% of its surface area as the liquid is drawn downward over the equilibration member by gravity. Liquid inlets may include liquid inlet nozzle(s) that direct the stream of incoming liquid at the equilibration member. The liquid stream may be introduced at a relatively slow rate such that gravity will substantially control the location where the liquid will strike the equilibration member. Alternatively, the liquid may be introduced as a stream that can be directed at the equilibration member by the liquid inlet (nozzle). In such embodiments, the liquid stream may be directed such that it will impact the surface at an angle that is perpendicular to the surface of the equilibration member at the point of impact.

In an embodiment, the introduction of liquid may be accomplished using a single liquid inlet (e.g., a liquid inlet nozzle) located at the point where the central axis of the chamber intersects the upper portion of the chamber wall. For example, where the chamber is a VRC or a spheroid, a single liquid inlet may be located at the center of the upper planar surface of the VRC or at the top of the spheroid respectively. The use of a single inlet located where the central axis of the chamber intersects the upper portion of the chamber wall permits the equilibrator to be operated when the central axis of the equilibrator (and the axis of rotation of the equilibration member) are displaced from 0° to about 15° or more from the vertical (e.g., the equilibrator may be tilted 0°-10° or 0°-15°) without disruption of its operation.

In other embodiments more than one liquid inlet (e.g., nozzle) may be located in the upper portion of the chamber such that water from one, two, three or more inlets is directed at the surface of the equilibration member. In one embodiment the inlets are spaced around (e.g., equidistant from) the point where the central axis of the chamber intersects the upper section of the chamber surface. Such embodiments include the placement of the liquid inlet at the corners of regular polygons (e.g., triangle, square, pentagon, hexagon, heptagon, or octagon) centered at the point where the central axis of the chamber intersects the upper section of the chamber surface. The liquid inlet(s), regardless of how they are arranged, may be placed in a portion of the chamber wall that is removably-resealable or in a portion of the chamber wall that is not removably-resealable with the portion of the chamber that retains the equilibration member. For example, where the chamber is substantially in the form of a VRC, all or part of the substantially planar upper surface of the VRC may act as a "lid" for the remainder of the chamber.

As the equilibrators are of a design that is substantially symmetrically about the central axis of the chamber, the equilibrator can be operated when the central axis is displaced from the vertical in any direction. As indicated above, the equilibrators may be operated when the central axis is displaced from about 0° to about 15° from the vertical. The use of higher liquid flow rates and/or liquid inlets with nozzles that direct liquid at the equilibration member increases the angle at which the equilibrator may be operated. In one embodiment the nozzles may extend into the chamber terminating proximate to the equilibration member such that they direct the incoming liquid at the equilibration member at an angle that is substantially normal to surface at the point where the liquid stream contacts the equilibration member. In some embodiments the equilibrator may be operated when the central axis is displaced (the equilibrator is tipped) up to about 20°, 25° or 30° from the vertical. The ability of the equilibrator to operate when tipped permits its use on, for example, floating platforms where waves may rock the equilibrator.

Liquid inlets and tubing bringing liquids to the inlets will typically have an inner diameter greater than 2 mm, for example in the range of about 2.0 to about 14.0 mm (e.g., 2.0-4.0, 2.0-6.0, 4.0-8.0, 6.0-10.0, 8.0-14.0. or 10-14 mm). Liquid inlets may terminate at or be in the form of a nozzle that extends into the chamber to direct the stream of incoming liquid at the equilibration member. Nozzles, when present, will be in the same size range as the tubing bringing liquid to the inlets, namely about 2.0 to about 14.0 mm (e.g., 2.0-4.0, 2.0-6.0, 4.0-8.0, 6.0-10.0, 8.0-14.0. or 10-14 mm). In an embodiment where the chamber is in the form of a VRC, the liquid inlets are placed on the substantially planar upper portion of the chamber and may be distributed as described above-with regard to the central axis.

One or more liquid outlets are located in the lower portion of the chamber and positioned to permit outflow of some or all of the liquid that collects in the lower portion of the chamber by gravity. Where the chamber is in the form of a VRC, the liquid outlet(s) may be in the cylindrical side wall of the chamber and/or in the substantially planar lower surface of the chamber. Where the chamber is spheroidal, ovoidal, or ellipsoidal, a single liquid outlet may be located at the point where the central axis of the chamber intersects the lower portion of the equilibrator chamber. In an embodiment, the chamber has the overall shape of a VRC, with the lower surface of the chamber modified either to a convex shape and/or to accommodate channels that direct liquids that are drawn to the bottom of the chamber by gravity toward one or more liquid outlets in the convex surface and/or in the channels.

Liquid inlets and the tubing carrying liquid away from the outlet will typically have an inner diameter of a similar size to the liquid inlet; however, where the liquid inlet is typically under pump pressure and the outlet passively drains liquid under the force of gravity, the diameters may deviate somewhat. More specifically, the liquid outlet will generally have an inner diameter greater than 2 mm, for example in the range of about 2.0 to about 20.0 mm (e.g., 2.0-4.0, 2.0-6.0, 4.0-8.0, 6.0-10.0, 8.0-14.0, 10-14, or 14-20 mm). During operation of the equilibrator the liquid outlet should not permit air to enter the chamber by allowing liquid to drain away too quickly, and at the same time liquid should not flood/overfill the chamber. Accordingly, the liquid outlet may be sized to maintain at least some liquid in the lower portion of the chamber. The cross sectional area of the liquid outlet, or a portion of the tubing attached to it may be adjustable and set to accommodate specific liquid out-flow rates by use of a valve or clamp that compresses/constricts the liquid outlet and/or the tubing attached to the outlet. Alternatively, a U-shaped liquid trap, a valve, a one-way flow valve (e.g., a check valve, flapper valve or feather valve) installed in the tubing that carrying liquid away from the equilibrator may be utilized to prevent air from entering the chamber through the liquid outlet.

Regardless of the shape of the chamber, placement of at least one of the one or more liquid outlets at or near the lowest point of the chamber (as determined when the central axis of the chamber is vertical) permits the clearance of solid/semisolid materials (e.g., sediment) from the chamber, which extends the time between cleanings necessary to maintain proper operation (gas equilibration). Where the equilibration member is positioned in the chamber by a ring, annular projection, or concave section formed in the lower portion of the chamber, any of those elements may be provided with channels, grooves or gaps so that liquid can reach the liquid outlet. The ring or annular projection may be of any suitable dimension. In an embodiment the ring will be formed from a hoop of a material (e.g., tubing) having a circular cross-section with a diameter of about 8 to 30 mm. Annular projections built into the wall of the chamber may be of similar size and shape to rings used to support the equilibration member (e.g. 0.7 to 2 cm in diameter/height). As with rings, annular projections built into the chamber wall used to support the equilibration member are provided with gaps or openings to permit the flow of liquids to and from the space below the equilibration member as needed, for example where the liquid outlet may be located. The equilibration chamber may be provided with external supports (e.g., external legs or a pedestal) to provide stability when placed on a horizontal surface and/or where the liquid outlet is located low enough on the chamber (e.g., on the bottom of a VRC chamber) that it would interfere with stable placement of the apparatus on a horizontal support surface.

One or more gas inlets are located in the wall of the lower portion of the chamber. Gas inlets are generally placed in the wall of the lower portion of the chamber at a point above the level of the liquid outlet(s). Placement in that manner is, however, not required provided that any mechanism used to introduce gas into the chamber provides sufficient pressure to prevent liquid in the chamber from backing up into the gas inlet(s) or the tube(s) supplying gas to the gas inlet(s).

Accordingly, in an embodiment, the gas inlet(s) may be place in the wall of the lower portion of the chamber at a point above the level of the liquid outlet(s) as determined when the central axis of the chamber is vertical. In another embodiment, the gas inlet(s) may be placed in the wall of the lower portion of the chamber above the level at which liquid can accumulate in the chamber as determined when the central axis of the chamber is 10°, 12°, 15°, 20°, 25° or 30° from the vertical, taking into consideration the location of the liquid outlet(s). In other embodiments the gas inlets are placed in the wall of the lower portion of the chamber at or below the level of the liquid outlet(s) as determined when the central axis of the chamber is vertical. In such an embodiment gas entering the chamber will bubble through the liquid as it enters.

Gas inlet(s) may terminate in a nozzle that diffuses the gas as it enters the chamber, or directs the gas entering the chamber in a specific direction. A combination of nozzles that diffuse gas or direct it in one or more directions may be employed. In an embodiment, where gas enters the chamber in a diffuse undirected fashion, it will cause turbulence in the gas in the lower portion of the chamber that may assist in the equilibration of the gases present in the liquid with the gas phase. In another embodiment, nozzles may direct a stream of gas entering the chamber toward the central axis of the chamber. In other embodiments, nozzles may direct gas entering the chamber away from the central axis of the chamber. For example, nozzles may direct gas entering the chamber along the interior surface of the chamber (parallel to the wall) at the point where the nozzle is located, thereby directing the gas in the lower portion of the chamber to circulate around the central axis.

Figure 7A:
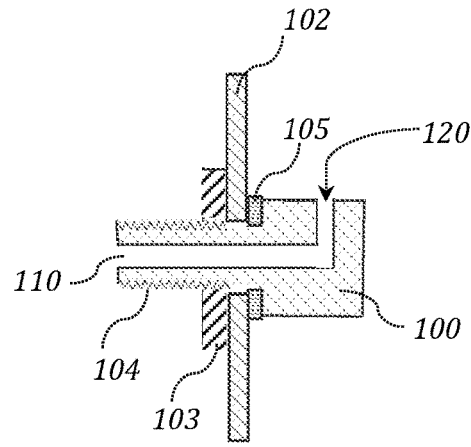
FIGS. 7A and 7B show in 7A a gas inlet nozzle 100, and in 7B a gas outlet with a shield 101. The inlet and outlet are shown in a portion of chamber wall 102 and are held in place by a retaining nut 103 that engages threaded section 104. When fully tightened, nut 104 causes compression of seal 105 providing a substantially gas and liquid tight seal. The nozzle shown in FIG. 7A has an internal pathway 110 through which gas may enter the chamber and be dispersed through nozzle end 120. The gas outlet shown in FIG. 7B has a shield section 101 that prevents droplets of liquid (e.g., water) from entering the entrance of the gas outlet 130, which is in gas communication with the internal passage 140 that forms part of the gas outlet.
Figure 7B:
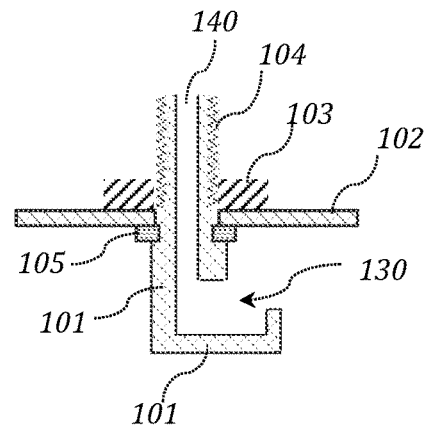
Figure 8:
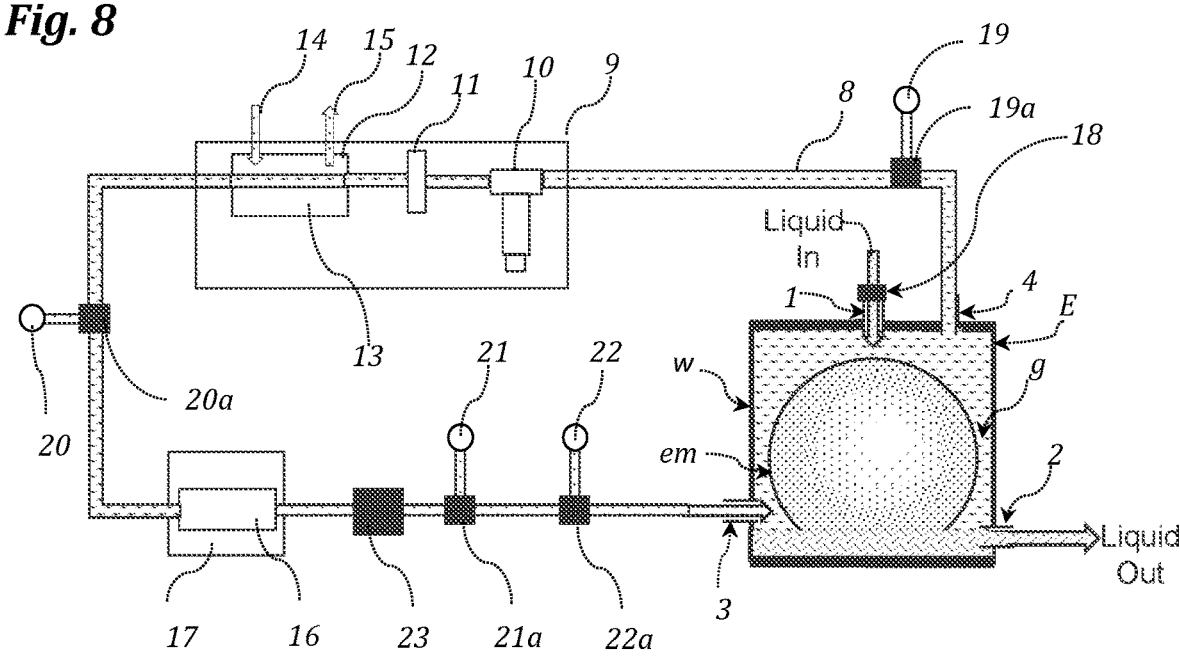
FIG. 8 shows a schematic of one configuration of a system that incorporates equilibrator (E). Various components of the system may be connected by wires or wireless communication components that are not shown. In addition, the sensor(s) (16) need not be encased in the analytical instrument.

One or more gas outlet(s) are located in the upper portion of the chamber's wall, and may be provided with a shield to prevent droplets of liquid that splash in their direction from entering the gas outlet (see FIGS. 7A and 7B). The gas outlets are positioned to avoid the intake of liquid, and accordingly, may be located in the chamber wall above the level of the liquid inlet(s). Where the liquid inlet(s) comprise a nozzle the extends into the chamber, the gas outlets may be located above the level where the liquid is discharged from the nozzle. Where the chamber is in, or substantially in, the form of a VRC, the gas outlets may be positioned on the substantially planar upper surface along with the liquid inlet(s). In an embodiment, the gas inlet(s) are located in a portion of the chamber wall that is removably-resealable with the portion of the chamber that retains the equilibration member. In such an embodiment, the removably-resealable portion of the chamber wall with the gas outlets may also contain one or more of the liquid inlets. Gas outlets also may be located in the upper portion of the chamber's wall that is not removably-resealable. In an embodiment, where the chamber is substantially in the form of a VRC, one or more of the liquid inlets and/or one or more of the gas outlets may be located in the substantially planar upper surface of the VRC, which acts as a "lid" for the remainder of the chamber.

The inner diameter of the gas inlets, and of the tubing connecting them, may be of any suitable size to accommodate the flow of gas to and from the chamber. In an embodiment, the inner diameter of gas inlets and outlets, and of the tubing connected to them, will be up to about 8 mm (e.g., up to about 6 mm or in the range of 4-8 mm) outside diameter with a wall thickness of about 0.5 mm or less giving an inside diameter up to about 7 mm (e.g. from about 3 mm to 7 mm) inside diameter. In other embodiments, the gas inlet(s), the gas outlet(s) and the tubing connected to them, each have an inner diameter selected independently from a range selected from: 1-12.5, 1-2, 2-4, 2-6, 2-8, 4-6, 4-8, 4-12.5, 6-10, 6-12.5 and 8-12.5 mm.

4. Materials for Chamber and Equilibration Member

The equilibrator apparatus may be constructed of any suitable materials. Generally, the materials used for construction, particularly of the equilibration member, are not porous and do not absorb water, as trapped water could interfere with gas exchange and/or increase the time required for the gas stream passing through the equilibrator to reflect the concentration of gases in the liquid being sampled (increase the response time of the equilibrator).

Generally the equilibrator components are constructed of a plastic (e.g., thermoset or thermoformed polymer) and/or metal that is selected independently for each component of the equilibrator. Such plastics include, but are not limited to, acrylonitrile butadiene styrene (ABS), acrylics (e.g., polymethyl methylacrylate), epoxy, polyamide (e.g., nylons), polycarbonate, polyester, polyether ether ketone (PEEK), polyetherketoneketone (PEKK), polyethylene (e.g., low density or high density polyethylene), polyethylene terephthalate, polypropylene, polystyrene, polysulfone, polyphenylsulfone, polytetrafluoroethylene (e.g., Teflon), polyvinyl chloride (PVC), polyurethane, urea formaldehyde, vinyl and combinations thereof. Metals that may be employed include, but are not limited to, aluminum, iron, steel, stainless steel, titanium, zinc, brass, or bronze and combinations thereof. Metal components may be coated with a polymer coating, an enamel coating, a sacrificial metal coating (e.g., zinc galvanizing), or a barrier metal coating (e.g. chrome) to avoid corrosion.

In an embodiment the chamber is formed from polypropylene and/or polyethylene and the equilibration member is formed from polypropylene and/or polyethylene or a metal such as steel that is coated to avoid corrosion. In such an embodiment, magnetic materials may be incorporated into the equilibration member to make it susceptible to magnetic localization inside of the chamber as discussed above.

Seals, which may be used, for example, in conjunction with removably-sealable portions of the chamber wall, and with gas and liquid inlets and/or outlets, can be formed from a variety of suitable materials. Materials suitable for forming seals include, but are not limited to, natural or synthetic rubbers (e.g., silicone rubber).

Long periods of exposure to daylight can negatively impact the equilibrator. Where plastics and/or rubbers or other materials that are susceptible to photo degradation/damage are used, they may include light stabilizers including, but not limited to, antioxidants, hindered amine light stabilizers, UV absorbers and the like. In addition, exposure to light permits the growth of algae and other organism, particularly when the liquid being tested is an aqueous liquid (e.g., fresh water, sea water and the like). Accordingly, plastics that are colored or contain fillers that substantially block or reflect light capable of supporting photosynthesis (e.g., from about 350 nm to about 750 nm) reduce the possible fouling of the equipment while extending the period between required service to keep the equilibrator clean and functioning properly. Coatings on the exterior of the chamber that reflect or absorb light can be used in place of colored plastics. Additionally, opaque fabric covers or shrouds can be used to protect equilibrator from harmful or photosynthesis promoting solar radiation.

Where water or other aqueous liquids are subject to measurement, the chamber may be made of materials that are hydrophobic and/or omniphobic, or coated with hydrophobic and/or omniphobic coatings, on all or part of the chamber's inner surface (all or part of the outer surface of the chamber may also be coated). Where non-aqueous liquids, or aqueous liquids having substantial amounts of other materials such as alcohols present, are subjected to measurement, omniphobic materials and/or omniphobic coatings may be utilized on all or part of the interior surface of the chamber (all or part of the outer surface of the chamber may also be coated). By controlling the hydrophobicity or omniphobicity of the chamber's inner surface (or the slide angle with, for example, aqueous test liquids), the response time of the equilibrator may be improved as droplets of liquid will not stick to the chamber walls, but will pass through the equilibrator. Another advantage of using a chamber with a hydrophobic or superhydrophobic inner surface is that such surfaces are considered "self-cleaning" as they resist the adherence of dirt and other materials/organisms that can foul the surface. Accordingly, the use of hydrophobic, superhydrophobic, or omniphobic surfaces extends the period of equilibrator operation between maintenance required to keep it functioning properly (indicated by maintaining the e-folding time to within 5%, 10%, 15% or 20% of the initial e-folding time established with an unfouled (clean) equilibrator operated under the same conditions (e.g., the equilibrator's initial e-folding time value or the e-folding time value after cleaning). Self-cleaning effects are most pronounced when the surfaces are omniphobic.

In contrast to the chamber's inside walls, where aqueous (or polar) liquids are being tested the equilibration member can be made hydrophilic, thereby encouraging the film of aqueous (or polar) liquid to spread over the equilibration member's surface increasing the surface area of the film and the exchange of gases.

In one embodiment, at least the interior surface of the chamber wall is made hydrophobic (or is made to have a low slide angle with water) and the equilibration member is made to have a hydrophilic surface. In another embodiment, at least the interior surface of the chamber wall is made superhydrophobic (or is made to have a slide angle with water less than) 5° and the equilibration member is made to have a hydrophilic surface. In another embodiment, at least the interior surface of the chamber wall is made omniphobic and the equilibration member is made to have a hydrophilic surface.

In an embodiment, all or part of the interior surface of the chamber (e.g. the interior chamber wall that can contact an aqueous test liquid) is hydrophobic and has a contact angle with water greater than about 90° (e.g., greater than about 100°, 110°, 120°, 130°, 140°, 150° or) 160°) at 22° C.

In an embodiment, the interior surface of the chamber (e.g. the interior chamber wall that can contact an aqueous test liquid) has a slide angle with water of less than about 30° (e.g., less than about 20°, 10°, or 5°) from the horizontal (level) at 22° C. For the purpose of this disclosure the slide angle for a material is the angle at which half of a set of ten water droplets, 25 microliters in volume, slide off or to the edge of a planar piece of the material as its incline is gradually increased from the horizontal (0°). For the purposes of this disclosure, a low slide angle is less than 10°.

Where the interior of the chamber is not already hydrophobic (e.g., constructed of a material with a suitable hydrophobicity), the surface of the equilibration member may be made hydrophobic or superhydrophobic by chemical treatment or by coating it with a hydrophobic coating. In one embodiment, all or part of the surface of the chamber (e.g., all or part of the inner surface of the chamber wall) is modified by treatment with hydrophobic silanizing agents (e.g., alkyl and fluoro alkyl silanizing agents). Hydrophobic silanizing agents include, but are not limited to: (tridecafluoro-1,1,2,2-tetrahydrooctyl) trichlorosilane; (tridecafluoro-1,1,2,2-tetrahydrooctyl) triethoxysilane; (tridecafluoro-1,1,2,2-tetrahydrooctyl) trimethoxysilane; (heptadecafluoro-1,1,2,2-tetrahydrodecyl)dimethyl(dimethylamino)silane; n-octadecyl-trimethoxysilane; n-octyltriethoxysilane; and nonafluorohexyldimethyhl(dimethylamino)silane. In other embodiments, all or part of the interior surface of the chamber may be treated with a hydrophobic coating to render the treated surfaces hydrophobic or superhydrophobic. Hydrophobic coatings include those with polyurethane, acrylic, and fluorovinyl (see, e.g., U.S. Pat. Nos. 5,962,620 and 9,067,821) polymer systems. Where it is desirable to have omniphobic behavior, the silanizing agents and/or coatings (e.g., the polymers of the coatings) should comprise fluoroalkyl groups.

In an embodiment, where the liquid subject to testing is an aqueous liquid, the surface of the equilibration member may be made hydrophilic. In such an embodiment, the contact angle of the equilibration member with water may be less than about 60° (e.g., less than about 50°, 40°, 30°, 20° or 10°) at 22° C. As discussed above, contact angles are measured using a goniometer.

If the equilibration member is not already hydrophilic (e.g., constructed of a material with a suitable hydrophilicity), the surface of the equilibration member may be made hydrophilic by chemical treatment or by coating it with a hydrophilic coating. In one embodiment, the hydrophilicity of the equilibration member is modified by treatment with hydrophilic silanizing agents. Hydrophilic silanizing agents include cyanomethyl, aminopropyl, and glycidoxypropyl silanes (e.g., cyanoethyltrimethoxysilane, aminopropyltriethoxysilane, and glycidoxypropyltriimethoxysilane). In another embodiment the surface of the equilibration member (e.g., rubber or plastic) may be treated with a plasma (e.g., oxygen plasma) to provide hydroxyl, carboxyl and carbonyl groups. In other embodiments oxygen plasma treated surfaces are subsequently treated with a nitrogen plasma to affix nitrogen containing groups to the surface and render it more hydrophilic. In other embodiments, all or part of the interior surface of the chamber may be treated with a hydrophilic coating (e.g., hydrophilic polyurethane, acrylic, or hydrogel compositions etc.) to render the treated surfaces hydrophilic (see, e.g., U.S. Pat. Nos. 5,962,620 or 6,017,577 describing hydrogels).

For the purpose of this disclosure, materials or surfaces are considered to be hydrophobic when the static contact angle of the surface with water at 22° C. is 90° or greater. Surfaces are considered to be superhydrophobic when the static contact angle with water at 22° C. is greater than 150°. Surfaces are considered omniphobic when they have a static contact angle with both water and hexadecane greater than 90° at 22° C. For the purpose of this disclosure, materials or surfaces are considered to be hydrophilic when the static contact angle of the surface with water at 22° C. is less than 90°. Contact angles are measured using a goniometer (e.g., Attension Model Theta goniometer, formerly KSV Instruments, available from BIOLIN SCIENTIFIC, Stockholm, Sweden according to the manufacturer's instructions.

5. Operation of the Equilibrator

In general terms, the equilibrator operates by having liquid introduced in the upper portion of the equilibrator chamber such that it contacts the equilibration member forming a film that is drawn downwards over the equilibration member (a falling film) to the lower portion of the chamber where it is directed to a liquid outlet and leaves the equilibrator. At the same time liquid is introduced into the upper portion of the equilibrator, a carrier gas is introduced into the lower portion of the chamber. Once introduced into the lower portion of the chamber, the incoming gas is displaced upward by the stream of incoming carrier gas. As carrier gas moves upward it contacts the falling film of liquid and the gases (e.g., carbon dioxide) in the liquid exchange into the carrier gas progressing toward equilibrium concentration as the liquid and carrier gas move in a counter current manner. The carrier gas, which is near or has reached equilibration with the gases in the incoming liquid, ultimately reaches the upper portion of the chamber where it exits the chamber via the gas outlet(s). After exiting the chamber via the gas outlet(s), all or part of the carrier gas is directed to the sensor of an analytical instrument (gas analyzer) that can measure the amount of the gas of interest in the carrier gas. Where the liquid is water or an aqueous solution, systems that incorporate the equilibrator with an analytical instrument may also have a dryer/dehumidifier interposed between the gas outlet(s) of the equilibrator and the sensor to remove from the carrier any gas liquid that condenses in the gas outlet line (sample gas line 8 connected to gas outlet 4) and/or any liquid (e.g., water) vapor before the carrier gas reaches the sensor 16 of the analytical instrument 17. Equilibrated sample gas(es) are pulled (slight vacuum) through the gas outlet line through the dryer/dehumidifier, and into/through the gas sensor by the intake side of a gas/air pump (e.g., a vane, fan, diaphragm etc.) 23 that is located downstream from the sensor. Carrier gas is directed from the pump outlet under positive pressure into the gas inlet line leading to the equilibrator. The dryer/dehumidifier will generally be placed "upstream" of the sensor of the gas analyzer when the system is operating in the forward direction (forward flow of causes carrier gas to move in the direction from the equilibrator's gas outlet toward the analytical instrument's sensor, reverse flow takes gas in the opposite direction toward the equilibrators gas outlet). The dryer/dehumidifier 9 may comprise one or more of a water trap 10, a filter 11 (e.g., a membrane filter made of paper, nylon, polyvinylidene difluoride (PVDF) and the like), and/or drying tube assembly 12. The drying tube assembly may comprise a dehumidifying Nafion© polymer tube 13 that is supplied with a flow of drying gas (e.g., air) through a drying gas inlet 14 and drying gas outlet 15 that has a lower amount of the water vapor such that it can dehumidify/dry the carrier gas stream coming from the equilibrator.

In an embodiment, carrier gas (e.g., air or an inert gas) exiting the chamber via the gas outlet(s), along with the gas of interest and liquid vapor (e.g., water vapor), is recirculated back to the gas inlet(s) after passing through one or more sensor of the analytical instrument 16 and the dryer/dehumidifier 9 if present. The gas may thus be kept in a closed loop except during periods when all or part of it is replaced or displaced by fresh carrier gas or when a gas standard is used to calibrate the analytical instrument. Analytical instrument 17 may contain a single type of sensor (e.g., $CO_2$) or multiple sensors arranged in parallel and/or in series that detect different species within the carrier gas stream (e.g., $CO_2$, methane, radon etc.). Accordingly, different species can be detected using the same equilibrated sample gas, either by placing sensors in series within a single gas train or in parallel where the gas train has been split after leaving the equilibrator and rejoined prior to entering the equilibrator gas inlet. In an embodiment, the analytical instrument contains at least a first sensor that is in arranged in parallel with a second sensor, and a third sensor in series with the first sensor.

Where the liquid subject to analysis forms as condensate (e.g., aqueous solutions or water), it may be desirable to periodically reverse the flow of gas in the line (tubing) attached to the gas outlet so that liquid that has been swept into and/or condensed in the lines is carried back into the chamber and to remove liquid from the dryer/dehumidifier 9. In some embodiments, the gas flow may be reversed through a segment of the line proximate to the gas outlet of the chamber 8 passing through the dryer/dehumidifier 9 (if present) and exhausted at port 19 or after passing through the chamber at port 22 (from sampling port 20 which is exhausted at port 19 or 22). In other embodiments, the flow may be reversed through both the dryer/humidifier 9 and the sensor 16 (e.g., gas low from sample port 21 which is exhausted at port 19 or 22). Valves 19a, 20a, 21a, and 22a are capable of connecting and closing off any combination of lines connected to them, but when measurements of a gas of interest in a liquid sample are being made they close off only the line to ports 19, 20, 21, and 22. Where gas circulation is reversed through the chamber it can be advantageous to stop the flow of liquid into the chamber during the period of reverse flow using a valve 18 upstream of liquid inlet 1.

Where gas flow is reversed for the purpose of clearing the gas lines of condensed liquids and/or drying the gas lines, previously unused carrier gas or gas used for standardization/calibration of the equipment (e.g., air or a gas with a known $CO_2$ or other gas species concentration) may be directed into the system (e.g., via a port 20 or 21) at one end of the section of the equipment to be dried and/or calibrated, and allowed to exit at a point downstream of the portion subject to drying and/or calibration.

In view of the foregoing, in one embodiment, an apparatus comprising an equilibrator as described herein may be operated to determine the amount of one or more gases of interest present in a liquid employing a method comprising the steps:

i) providing an apparatus of any one of embodiments 1-25 (enumerated below);

ii) introducing the liquid into the chamber of the apparatus by way of the liquid inlet such that it passes over the equilibration member and exits the apparatus by way of the liquid outlet;

iii) directing a carrier gas into the apparatus by way of the gas inlet such that it flows over the equilibration member in a direction that is counter current to the flow of the liquid and exits the chamber of the apparatus by way of the gas outlet;

iv) directing all or part of the gas that exits the chamber to a sensor of an analytical instrument that determines the amount of the gas or gases of interest present in the liquid; and v) determining the amount of a gas or gases of interest present in the liquid based on the output of the detection system.

In some embodiments, in addition to the equilibrator, the sensor of the analytical instrument, and an optional dryer/dehumidifier, the system may comprise an auto-controlled drying mechanism and carrier gas (e.g., atmospheric gas/air) sampling port circuit composed of a combination of solenoid and valves (e.g., one-way valves) and an electrical relay to simultaneously stop water pumping into the equilibrator. In such embodiments, the method may further comprise the steps of sampling carrier gas (e.g., air from the atmosphere) through the carrier gas sampling port (by opening a valve to that port) and directing it to the sensor for measurement/calibration purposes, after which it is exhausted toward the equilibrator through the same sample gas line that connects the gas out of the equilibrator chamber to the sensor system. By doing so, the line that normally brings gas laden with liquid vapor (e.g., water vapor) from the equilibrator to the sensor system can be cleared of accumulated liquid that has, for example, condensed in the line and the sensor system. By directing carrier gas from the sampling port that is not saturated with liquid vapor (e.g., water vapor) through the dryer/dehumidifier, the dryer/dehumidifier apparatus and/or any chemical drying agents it contains may be fully or partially regenerated. Alternatively, the chemical drying agent may be contained in a chamber equipped with a heating element and may be periodically regenerated by heating the drying agent if the apparatus is located where energy consumption of the drying process can be provided. In an embodiment, samples of the chemical drying agent are replaced periodically at times determined by the climate/ambient relative humidity and temperature instead of being regenerated.

The frequency with which the flow of gas is reversed to remove all or part of the liquid that might accumulate in the lines (tubing) carrying gas from the equilibrator to the sensor system can vary depending on a variety of factors. Fluid accumulation in the line leading from the gas outlet of the chamber to the sensor is often the result of condensation of vapor from the fluid being sampled becoming part of the carrier gas stream. Accordingly, the temperature of the fluid, which will change its vapor pressure, and the temperature of the line, which is largely dictated by ambient temperature of the location where the sensor part of the system is installed, may in large part dictate the need for clearing the line of fluid. In embodiments, the direction of gas flow is reversed to clear the lines during less than 25% (e.g., less than 20, 15, 10 or 5%) of its operating time. By way of example, a system encompassing the equilibrator may have the direction of gas flow reversed for a continuous period of 15 minutes every one, two, three, four, five, or six hours. Under field conditions, 15 minutes per six hours operating time is often sufficient and provides the opportunity to measure ambient atmospheric gas concentrations (e.g., ambient $pCO_2$ values).

As discussed above, the equilibrator functions by permitting the exchange of the gas of interest between the film of fluid being drawn downward over the equilibration member (falling film) and the gas moving up through the equilibrator. Accordingly, efficient exchange requires the film of liquid have sufficient area. At the same time, the gas flow should be sufficient to provide a suitable response time, but not so fast as to cause turbulence in the equilibrator (e.g., turbulence that carries water droplets into the gas outlet(s)). The flow of liquid into the equilibrator required to provide a film of sufficient area depends on many factors including, but not limited to, the shape of the equilibration member, its dimensions (including surface area), the viscosity of the liquid, and the interaction between the liquid and the surface (e.g., is there enough interaction energy between the surface and the liquid for efficient wetting). In general, falling films are initiated with liquid of sufficient volume that is injected with some positive pressure onto the top surface of the equilibration member to completely wet the surface of the equilibration member and to maximize the integrated wetted surface area over time. Larger equilibration members will have more instantaneous wetted surface area than smaller equilibration members.

In an embodiment, the flow of liquid required to maintain a falling film over the surface of the equilibration member may vary from about 0.25 liters/minute (l/min) to about 12 l/min (e.g., 0.25-1, 0.25-2, 1-4, 2-6, 4-8, 6-12 or 8-12). Exact flow rates will be limited by the equilibrator member surface area and drain diameter, and thus may have potential for broad working range. Lower flow rates, such as 0.25 or 1.0 l/min, are useful with smaller equilibration members (e.g., those with surface areas of less than 1000 $cm^2$) and higher flow rates, such as 6-12 or 8-12 l/min, with larger equilibration members (e.g., those with surface areas of 1000 $cm^2$ or greater).

Gas flow rates through the chamber during operation necessary to obtain measurements will vary depending on a variety of factors including, but not limited to, the interior volume of the chamber, the shape of the chamber, and the desired response time of the apparatus to changes in the content of a gas of interest in the liquid being sampled. In an embodiment, the gas flow may vary from about 0.25 liters/minute (l/min) to about 3 l/min (e.g., 0.1-1, 1-2, or 2-3 l/min). Flow rates (e.g., in $cm^3$/min.) may be adjusted based on the chamber's headspace (interior volume not occupied by the equilibration member or support structures such as annular rings and/or pedestals), with lower flow rates of about 0.08 to about 2.5 $cm^3$ of carrier gas per $cm^3$ of headspace per min. (e.g., from about 0.08 to about 0.2, about 0.2 to about 0.5, about 0.5 to about 1.0, about 1.0 to about 2.0, or from about 2.0 to 2.5 $cm^3$ of carrier gas/($cm^3$ of headspace) per minute).

For operation the equilibrator apparatus described herein can be mounted to a stationary mount. Alternatively, because the equilibrator can operate when tipped at moderate angles, it can be mounted on a mobile platform such as a boat, buoy, raft or similar platform permitting a range of installation options for measuring gases of interest. The equilibrator is not disturbed by bubbles or particulates small enough to pass through the lines/nozzles used to deliver liquids to the chamber and/or the fluid outlet and lines that carry liquid away from the equilibrator's chamber.

Because various gas species are produced through both natural and engineered processes, measurements of gas concentration is important for understanding many aspects of water quality. There are many applications for equilibration and measurement that address both environmental and human health issues. Virtually any gas species that can be absorbed in water (natural surface waters, pore water, groundwater/aquifer, or water within engineered water systems such as well water, waste water treatment facilities, drinking water treatment plants, swimming pools, algal photobioreactor systems used for carbon capture and sequestration, etc.) can be equilibrated or substantially equilibrated with carrier gas or air in the headspace (the chamber's interior volume not occupied by the equilibration member and any supports, such as pedestals or annular rings, used to support the equilibration member) of the falling film equilibrators described herein regardless of the relative solubility of the gas. Gas species can then be measured by use of the appropriate analytical instrument and sensor (e.g., NDIR, photo-acoustic detectors, gas chromatographs, radiation such as alpha particles) in either real time or as discrete samples.

Among the gases that could be measured using the falling film equilibrators described herein are ammonia, $CO_2$, CO, sulfur oxides (e.g., sulfur dioxide), nitrogen oxides (e.g., NO or $NO_2$), methane, ethane, hydrocarbons, halogenated hydrocarbons, chlorofluorocarbons (CFCs), hydrofluorocarbons (HFCs), perfluorocarbons (PFCs), esters, sulfur hexafluoride ($SF_6$), chlorine, bromine, radon, hydrogen sulfide ($H_2S$), HF, HCl, HBr, and HI. Measurements can be made, for example, of one, two, three or more of such gases. By way of example, measurement of $CO_2$ can be made by infrared detection and measurement of radon by using a detector for alpha-radiation. Some gases/volatile materials particularly relevant to human health and/or of environmental concern that can be measured in, for example, aqueous samples using the falling film equilibrator described herein include carbon dioxide, methane, radon, hydrogen sulfide, halogenated alkanes (e.g., trihalomethanes), sulfur hexafluoride, nitrous oxide, and sulfur dioxide.

Carbon dioxide ($CO_2$) can be measured to determine its concentration as related to carbonate chemistry (the chemistry of ocean acidification comprised of total dissolved inorganic carbon, carbonate, bicarbonate, pH, total alkalinity, etc.), $CO_2$ sources/sinks (e.g., estuaries, rivers, streams), $pCO_2$/pH control (e.g., monitoring and control of pH in swimming pools), ecosystem metabolism (e.g., photosynthesis/respiration patterns), and carbon capture/sequestration in industrial settings, and in understanding greenhouse gas effects.

Methane ($CH_4$) is an important gas to monitor as it is both a greenhouse gas with 25× forcing potential than $CO_2$ and explosive if it builds up to significant levels. Methane can occur in drinking water, waste water, groundwater/aquifers, pore water in natural aquatic systems (e.g., lakes, rivers, streams, wetlands), in engineered environments such as industrial ponds, and in water released from industrial processes and engineered environments. Sources of methane include industrial (e.g., petroleum) processing, natural gas release, and agricultural sources (livestock and manure).

Radon (Rn) is a human health hazard linked to the development of lung cancer produced naturally via the radioactive decay of uranium in bedrock and occurs in well water, aquifers, rivers, the sump of numerous homes, etc.

Hydrogen sulfide ($H_2S$), is a poisonous, corrosive, flammable gas produced by anaerobic microbial decomposition of organic materials in wetlands and sewers, and also occurs in natural gas and volcanic gases.

Halogenated alkanes, including total trihalomethanes (e.g., chloroform ($CHCl_3$), bromoform ($CHBr_3$), dibromochloromethane ($CHBr_2Cl$), and bromodichloromethane ($CHBrCl_2$), are a human health hazard due to their toxicity. Trihalomethanes are common water disinfection byproducts resulting from water chlorination. While the concentration of halogenated alkanes is regulated in drinking water, they occur commonly in swimming pools.

Sulfur hexafluoride ($SF_6$), which is used as a tracer gas and an electrical insulator, represents a substantial environmental hazard. Sulfur hexafluoride is one of, if not the, most potent greenhouse gas, as evaluated by PICCC (Primary Industries Climate Challenges Centre) having 22,000× forcing potential of $CO_2$.

Nitrous oxide ($N_2O$) is an environmentally hazardous material that can contribute to greenhouse warming (298× forcing potential of $CO_2$). Nitrous oxide is produced naturally by microbial processes in soils, manure, and the ocean. The gas also results from anthropogenic sources such as fertilized soils. It is used extensively as an aerosol propellant, in medical and dental procedures as an anesthetic, and as a supplementary oxidizer for internal combustion engines and in rocket fuel.

Sulfur dioxide ($SO_2$) is a major air pollutant that impacts human health. It is a precursor to inorganic acids and a component of acid rain. Sulfur dioxide has its environmental origins in volcanic sources and in the industrial combustion of sulfur containing materials.

A large variety of liquids can be assessed for the levels of dissolved gases and/or volatile components including salt water, sea water, brackish water, tidal water, marsh water, river water, lake water, stream water, spring water, ground water, aquifer water, pore water, geyser water, volcanic water, well water, swimming pool water, aquarium water, sewage (e.g., sewer water), industrial waste streams, industrial waste water, irrigation water, run-off from agricultural sites, run-off from mines, run-off from industrial sites, drinking water, treatment plant water, and treated sewer water.

The design of the equilibrator permits monitoring of one or more gas species in a continuous or semi-continuous fashion (continuous, except during intervals where the equilibrator is operated with gas flow in the reverse direction to clear liquid) as opposed to taking discrete samples which are subject to analysis. It is also possible to incorporate additional sensors into the equilibrator or the adjacent analytical equipment to measure the characteristics of the fluid being measured such as temperature and pH, which can be measured in the body of liquid subject to testing, in the chamber, or in the lines (tubing) connected to the equilibrator.

Operation of the equilibrator and the system it is connected to for the analysis of gases of interest in liquid samples requires controlling the flow of both liquids and gases. Liquids may be direct to flow by the use of any suitable pump including, but not limited to, vane, impeller, piston, centrifuge and diaphragm pumps, any or all of which may be reversible. Similarly, the flow of gases may be directed by the use of pumps including, but not limited to, vane, impeller, piston, centrifuge, bellows and diaphragm pumps, any or all of which may be reversible. Gases may also be directed to flow by use of a source of previously compressed gas (e.g., a pressurized tank) or by the application of reduced pressure (vacuum or partial vacuum). In operation, the movement of gases may be directed in a system incorporating an equilibrator using any combination of pumps, vacuum and compressed gas sources.

CERTAIN EMBODIMENTS

1. An apparatus comprising:
   a chamber comprising an outer wall that is disposed substantially symmetrically about a central axis, the outer wall defining the interior surface of the chamber, the exterior surface of the chamber, and space within the chamber;
   an equilibration member within the chamber having an equilibration member surface, an axis of rotation, and a bisecting plane perpendicular to the axis of rotation positioned at the midpoint of the equilibration member's axis of rotation;
   the equilibration member being positioned within the chamber such that its axis of rotation and the central axis of the chamber coincide or substantially coincide;
   the chamber, the exterior surface of the chamber, the interior chamber wall, the equilibration member within the chamber, and the space within the chamber being divided into an upper portion above the bisecting plane and a lower portion below the bisecting plane;
   the space within the upper portion of the chamber being in liquid (fluid) and gas communication with the space within the lower portion of the chamber via one or more gaps between the equilibration member and the interior chamber wall;

a liquid inlet located in the upper portion of the chamber positioned such that a liquid introduced into the chamber from the liquid inlet contacts the upper portion of the outer surface of the equilibration member;

a liquid outlet located in the lower portion of the chamber positioned to permit outflow of some or all of the liquid introduced into the chamber that collects in the lower portion of the chamber by gravity;

a gas inlet located in the wall of the lower portion of the chamber; and a gas outlet located in the wall (e.g., in the is removably-resealable portion of chamber) of the upper portion of the chamber;

wherein at least a section of the upper portion of the chamber wall is removably-resealable to the remainder of the upper surface and/or the outer wall.

2. The apparatus of embodiment 1 wherein the equilibration member is selected from the group consisting of: a spheroid; an ellipsoid, an ovoid; a hemisphere; a hemiellipsoid; a hemiovoid; a domed frustum; a series (two, three, four, or more) of spheres or disks aligned along the central axis (see, e.g., FIGS. 5A-5N and 6A-6N); a column; a column having one, two, three, four, or more spiral grooves; a column having sinusoidal oscillating sides; a cone having one, two, three, four, or more spiral grooves; and a cone having sinusoidal oscillating sides.

3. The apparatus of any preceding embodiment wherein the interior and/or exterior surface of the chamber is substantially in the form of a vertical right cylinder, a sphere, an ellipsoid, or an ovoid.

4. The apparatus of any preceding embodiment, wherein the chamber is a substantially vertical right cylinder (VRC) wherein the wall forms an upper and a lower surface positioned substantially perpendicular to the central axis of the chamber.

5. The apparatus of any preceding embodiment, wherein the section of the upper portion of the wall that is removably-resealable forms a lid on the remainder of the lower portion of the chamber, wherein when the chamber is a VRC with an upper surface positioned substantially perpendicular to the central axis of the chamber, the lid comprises all or part of the upper surface.

6. The apparatus of embodiment 5, wherein the liquid inlet and/or gas outlet are positioned in the lid.

7. The apparatus of any preceding embodiment, wherein the liquid inlet is positioned either at, or proximate to, the central axis.

8. The apparatus of any preceding embodiment, wherein when the chamber is a VRC with a lower surface positioned substantially perpendicular to the central axis of the chamber the liquid outlet and/or the gas inlet are positioned in the lower surface of the chamber.

9. The apparatus of any preceding embodiment, wherein the liquid outlet is positioned in the lower portion of the outer wall of the chamber; wherein the liquid outlet is of an adjustable diameter to accommodate a range of liquid flow rates, and wherein liquid flowing through the outlet creates a seal that limits gas from entering or exiting the equilibrium chamber by way of the liquid outlet thereby forming a self-correcting pressure seal that equalizes the interior and exterior pressure to substantially match ambient barometric pressure.

Figure 1:
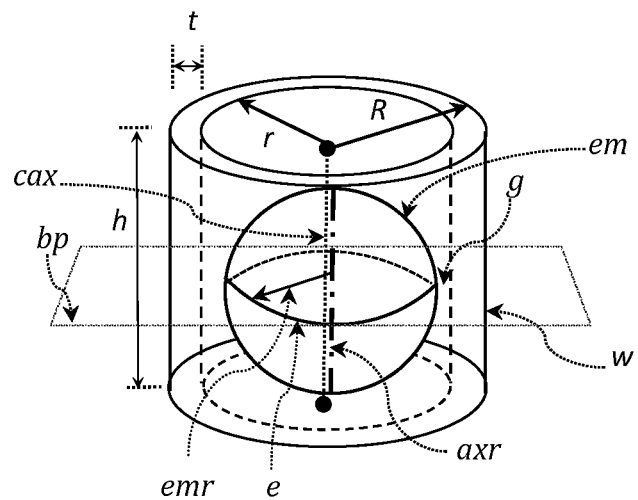
FIG. 1 shows an illustration introducing the general terminology for the falling film gas liquid equilibrators described herein using an equilibrator with a substantially cylindrical chamber having a height h at the central axis cax ( - - - - ), an inner radius r, an outer radius R, and a wall w of thickness t. The equilibrator is shown as having a substantially spherical equilibration member em with an axis of rotation axr ( – – – – ) having a length substantially equal to the height of the em, and a maximum radius emr, appearing, in this instance, at the equator e of the sphere. As the emr is less than the inner radius r, a gap g is shown between the inner surface of the w and the surface of the em. In the illustration the cax and the axr are substantially aligned. The drawing is not to scale.
Figure 2:
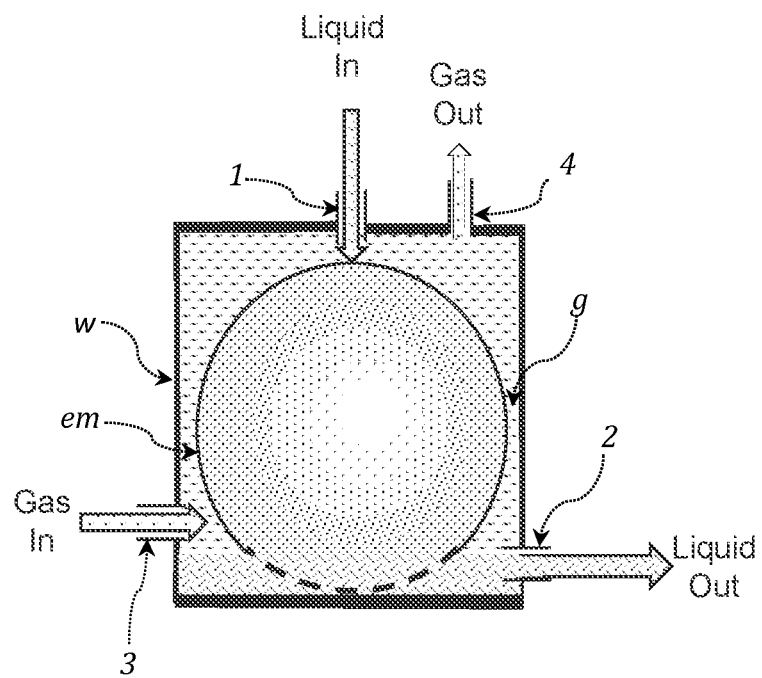
FIG. 2 shows a schematic cutaway of an equilibrator with a substantially cylindrical chamber with a wall w showing its spherical equilibration member em and a gap g between w and em. The schematic shows the liquid inlet 1, liquid outlet 2, gas inlet 3, gas outlet 4, liquid is denoted by the wavy lines  and gas by the dashes .

10. The apparatus of embodiment 9, wherein the gas inlet 3 is positioned in the wall of the chamber w at a level between the bisecting plane of the equilibration member when located in the chamber and a plane that is perpendicular to the central axis and parallel to a plane passing through the liquid outlet 2 (see, e.g., FIG. 2 or 3).

11. The apparatus of any preceding embodiment, wherein the gas outlet is positioned in the removably-resealable portion of the chamber wall (e.g., in the flat upper surface of a VRC lid).

12. The apparatus of any one of embodiments 1-10, wherein, when the chamber is a VRC, the gas outlet is not located in the removably-resealable portion of the chamber wall.

13. The apparatus of any preceding embodiment, wherein the liquid inlet comprises a liquid inlet nozzle (e.g., a piece of tubing) that extends into the chamber.

14. The apparatus of any preceding embodiment, wherein the liquid inlet nozzle extends into the chamber at a level that is between the upper surface (top moist point) of the equilibration member and a plane that is parallel to the bisecting plane and passes through the gas outlet.

15. The apparatus of any preceding embodiment, wherein the surface of the equilibration member is not porous and/or does not absorb water.

16. The apparatus of any preceding embodiment, wherein the surface of the equilibration member is hydrophilic.

17. The apparatus of any preceding embodiment, wherein the interior surface of the chamber has a contact angle with water greater than about 70°, 80°, 90°, 100°, 110°, 120°, 130°, or 140° at 22° C.

18. The apparatus of any preceding embodiment, wherein the interior surface of the chamber has a slide angle with water less than about 30°, 20°, 10°, or 5° at 22° C.

19. The apparatus of any preceding embodiment, wherein the gas inlet comprises an opening that directs the incoming gas in the direction of the central axis or into a plane that is perpendicular to the central axis of the chamber.

20. The apparatus of any of embodiments 1-15, wherein the gas inlet comprises an opening that directs the incoming gas substantially in a plane that is perpendicular to the central axis (e.g., forcing the gas to circulate in a clockwise or counter clockwise fashion with the chamber).

21. The apparatus of any preceding embodiment, wherein:
   i) the equilibrium member is free to floating on liquid that accumulates in the lower portion of the chamber (the accumulated liquid acts as a liquid bearing and the equilibrium member may freely rotate under the force of the liquid entering the chamber such as via the inlet nozzle(s) described in embodiments 13 and 14); or
   ii) the apparatus further comprising an annular element within the chamber in contact with the lower portion of the chamber (e.g., the substantially planar lower surface of a VRC) and the equilibration member.

22. The apparatus of any preceding embodiment, wherein the equilibration member comprises a magnet or a magnetically susceptible material, and wherein the apparatus further comprises a magnet or magnetically susceptible material positioned on or in the chamber wall so as to magnetically engage the equilibration member (e.g., hold the member in position within the chamber by contacting the member to the chamber wall or proximate to the chamber wall).

23. The apparatus of embodiment 22, wherein when the equilibration member is magnetically engaged it is positioned proximate to, but not in direct contact with, the lower portion of the chamber wall (e.g., when the chamber is a VRC the equilibration member is held against a support such as the annular element of embodiment 21 which is in contact with the substantially planer lower surface of the cylinder).

24. The apparatus of any one of embodiments 22 or 23, wherein the central axis of the chamber passes through the magnet or magnetically susceptible material positioned on or in the wall of the chamber.
25. The apparatus of any preceding embodiment, wherein the volume of the chamber is less than 2.5 times (e.g., less than 2.25, 2.0, 1.75, 1.6, 1.5, 1.4, 1.3, 1.2 or 1.1 times) the volume of the equilibration member.
26. A method of determining the amount of a gas or gases of interest present in a liquid comprising the following steps:
    i) providing an apparatus of any one of embodiments 1-25;
    ii) introducing the liquid into the chamber of the apparatus by way of the liquid inlet such that it passes over the equilibration member thereby forming a falling film over all or part of the equilibration member's surface, and exits the apparatus by way of the liquid outlet;
    iii) directing a carrier gas into the apparatus by way of the gas inlet such that it flows over the equilibration member in a direction that is counter current to the flow of the liquid and exits the chamber of the apparatus by way of the gas outlet;
    iv) directing all or part of the gas that exits the chamber to a sensor of an analytical instrument that determines the amount of the gas or gases of interest present in the liquid; and
    v) determining the amount of a gas or gases of interest present in the liquid based on the output of the detection system.
27. The method of embodiment 26, wherein the carrier gas is selected from the group consisting of air, nitrogen, an inert gas (e.g., argon, neon, xenon, or helium), hydrogen, oxygen or a mixture of any thereof.
28. The method of any one of embodiments 26 to 27, wherein at least one of the gas or gases of interest is selected from the group consisting of ammonia, $CO_2$, CO, sulfur oxides (sulfur dioxide), nitrogen oxides (e.g., NO or $NO_2$), methane, ethane, hydrocarbons, halogenated hydrocarbons, chlorofluorocarbons (CFCs), hydrofluorocarbons (HFCs), perfluorocarbons (PFCs), esters, sulfur hexafluoride ($SF_6$), chlorine, bromine, radon, hydrogen sulfide ($H_2S$), HF, HCl, HBr, and HI.
29. The method of any one of embodiments 26 to 28, wherein the gas of interest is $CO_2$.
30. The method of any one of embodiments 26 to 29, wherein the liquid comprises water.
31. The method of any one of embodiments 26 to 30, wherein the liquid is selected from the group consisting of: salt water, sea water, brackish water, tidal water, marsh water, river water, lake water, stream water, spring water, ground water, aquifer water, pore water, geyser water, volcanic water, well water, swimming pool water, aquarium water, sewer water, industrial waste water, irrigation water, run-off from agricultural sites, run-off from mines, run-off from industrial sites, drinking water treatment plant water, and sewage treatment water.
32. The method of any one of embodiments 26 to 31, wherein the liquid comprises water, and wherein directing all or part of the gas that exits the chamber to a detection system further comprises providing a dryer/dehumidifier positioned between the gas outlet and the detection system, the dryer/dehumidifier receiving all or part of the gas that exits the chamber and removing all or part of the water vapor from the gas exiting the chamber to produce a dried gas stream, the detection system receiving all or part of the dried gas stream.
33. The method of any one of embodiments 26 to 32 further comprising step (vi):
    vi) for a period of time flowing gas through the sensor and/or dryer/dehumidifier to remove all or part of the condensed liquid vapor (e.g., water vapor) that may have condensed in the sensor and/or dryer/dehumidifier, or in the lines connected thereto.
34. The method of any one of embodiments 26 to 33, wherein the apparatus further comprises an auto-controlled drying mechanism comprising a sampling port circuit composed of a combination of solenoids, valves, and a mechanism (e.g., relay, sensor, and/or switch) to stop liquid pumping into the chamber, the method further comprising:
    stopping test liquid (e.g., water) from flowing into the equilibrator,
    operating the auto-controlled drying mechanism to cause carrier gas flow from a port [which can draw or vent a gas to the atmosphere (air), a carrier gas source, and/or calibrator gas source such as ports 20 or 21] through the dryer/dehumidifier 9, or the dryer/dehumidifier 9 and the sensor 16, toward the equilibrator (e.g., reverse flow) through a sample gas line 8 (which during forward flow brings gas from the equilibrator to the sensor system); and
    exhausting the gas flowing from the port after passing through the dryer/dehumidifier, or the dryer/dehumidifier and the sensor, through a port 19 prior to reaching the equilibrator E and/or after passing through the equilibrator chamber 22. (Passing carrier gas through the parts of the system including the gas sample line, and exhausting the gas once laden vapors of condensed liquid, removes condensation in the gas sample line between the equilibrator and the sensor system, thereby preventing system failure due to condensed liquid (e.g., water) entering into the sensor system.)
35. The method of any one of embodiments 26 to 34, wherein during the period when a carrier gas (e.g., air and/or calibrator gas) is flowing (e.g., from a port such as 20 or 21) through the sensor 16, establishing a baseline measurement and/or calibration measurement.
36. The method of embodiment 35, wherein the calibrator gas is air and the flow of liquid is stopped at the liquid inlet.
37. The method of embodiment 35, wherein the calibrator gas has a defined amount of $CO_2$ and the flow of liquid is stopped at the liquid inlet.
38. The method of any one of embodiments 26 to 37, further comprising:
    providing a gas with a known amount of the gas of interest;
    introducing said gas with a known amount of the gas of interest into the gas inlet (e.g., through port 22) and passing it through the equilibrator (and the dryer/dehumidifier if present) and the sensor, and then exhausting it from the system after passing through the sensor (e.g., through port 21) (alternatively, introducing said gas with a known amount of the gas of interest into the sensor (e.g., through port 19 or port 20) and exhausting it from the system after passing through the sensor (e.g., through port 21)); and
    calibrating and/or confirming the calibration of the detection system while the gas with a known amount of the gas of interest is present in and/or flowing through the sensor.

39. The method of any one of embodiments 26 to 34, further comprising:
    providing a liquid with a known amount of the gas of interest,
    introducing said liquid with a known amount of the gas of interest into the liquid inlet; and
    calibrating and/or confirming the calibration of the detection system while the liquid with a known amount of the gas of interest is flowing through the equilibrator.

EXAMPLES

Example 1. Comparison of Equilibrators with 20 and 25 cm Diameter Equilibration Members Two equilibrators having spherical equilibration members placed inside VRC chambers with a single fluid inlet in the center of their removable planar upper surface and outlet on the cylindrical surface about 1-1.5 cm from the bottom of the chamber were prepared (see, e.g., FIG. 3). The first equilibrator had an equilibration member had a spherical equilibration member about 20.3 cm (about 8 inches) in diameter with a chamber volume of about 7.57 liters (about 2 gallons). The second equilibration member had a spherical equilibration member about 25.4 cm (about 10 inches) in diameter with a chamber volume of about 13.25 liters (about 3.5 gallons).

Using a semi-enclosed 400 liter tank, water was pumped from the bottom of the tank into the tops of the two falling film equilibrators in parallel and at similar flow rates. $CO_2$ concentrations in the test tank were manipulated by either spiking with pure $CO_2$ gas momentarily, or by continual bubbling with $CO_2$—stripped gas to drive $CO_2$ concentrations downward. Water flow rates ranged from approximately 50 to 100 gallons per minute. Water draining out the bottom of the equilibrator were directed back into the tank and were recirculated. At any time, one or the other of the paired equilibrators was connected via a valve system to a closed loop gas train that led out of the top of the equilibrator chamber, through a dehumidifying apparatus, into a LI-COR LI-7000 infrared $CO_2/H_2O$ gas analyzer and back into the bottom of the equilibrator. Air was used as the carrier gas and was circulated in the closed loop gas train at a rate of 1 liter per minute. Readings of $pCO_2$ were logged at 1-min intervals. The gas train was switched rapidly to alternately monitor the gas flow and determine how closely two equilibrators of different size agreed with one another when challenged with water of the exact same $CO_2$ content and to observe how quickly they responded to changes in dissolved gas ($CO_2$).

Figure 9:
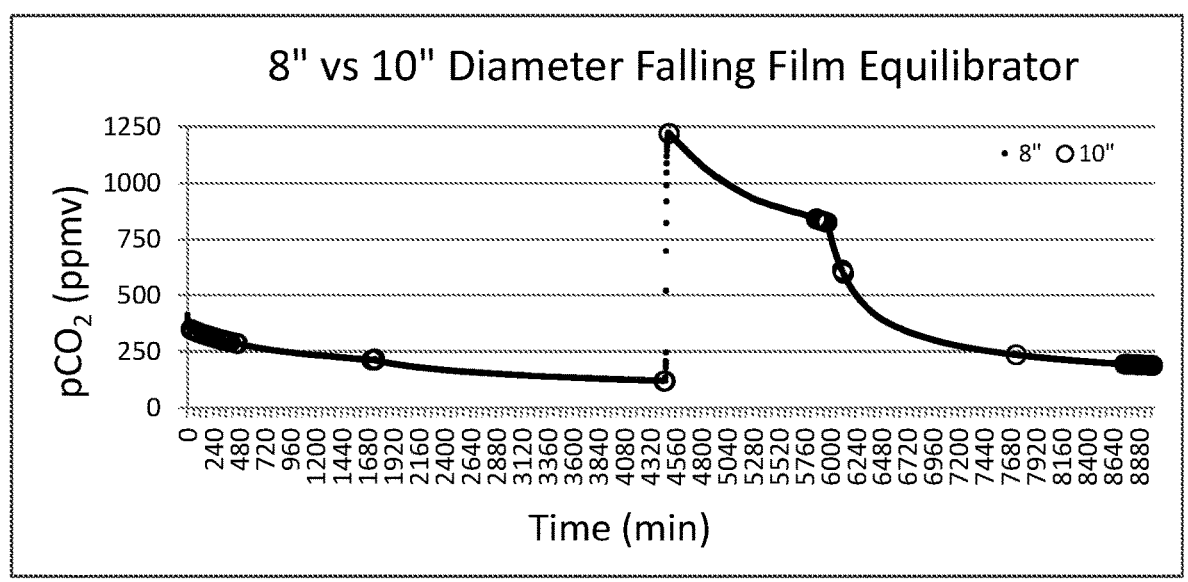
FIG. 9 shows a performance comparison of equilibrators having an 8-inch diameter spherical equilibration member with an equilibrator having a 10-inch dimeter equilibration member over a 6-day period in a dynamic $pCO_2$ test as described in Example 1. Measurement values taken from the equilibrator having an 8-inch diameter spherical equilibration member are shown as a filled dot "•", and those taken with the equilibrator having a 10-inch dimeter equilibration member are shown as an open circle "○". Similar results are obtained down to about 3.7-inch diameter spherical equilibration members.
Figure 10A:
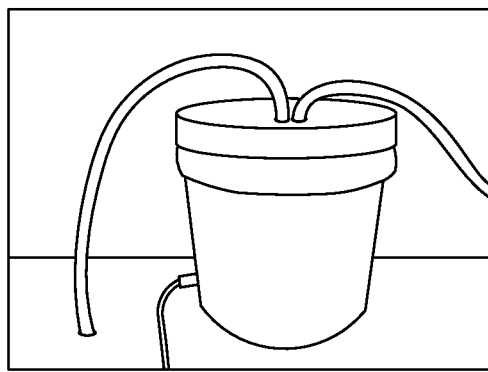
FIGS. 10A-10F show six photographs of a spherical falling film equilibrator apparatus of the type shown schematically in FIG. 3 and used in Example 1 (10-inch diameter equilibration member) having a 13.25 liter chamber that is substantially a virtual right cylinder (VRC)
Figure 10B:
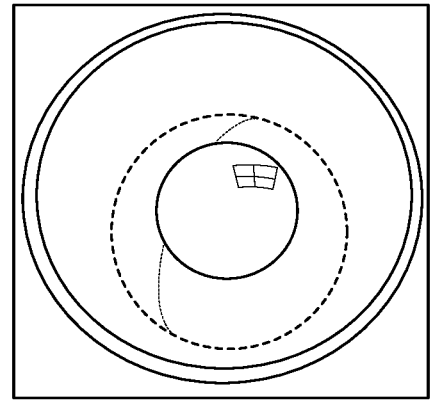
Figure 10C:
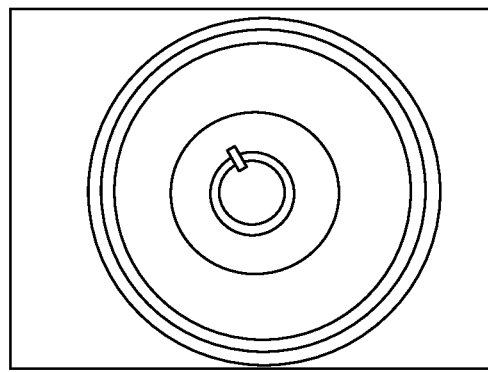
Figure 10D:
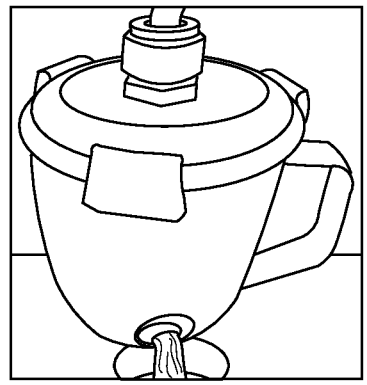
Figure 10E:
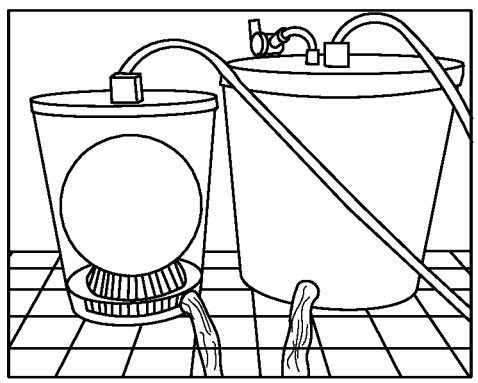
Figure 10F:
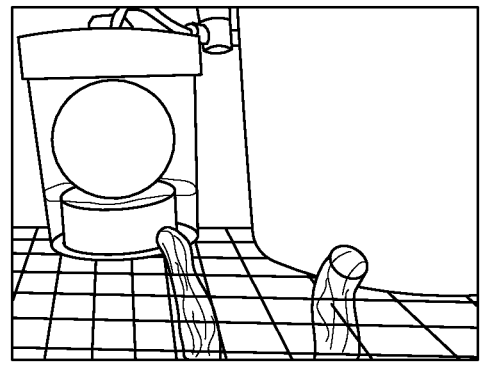
Figure 11A:
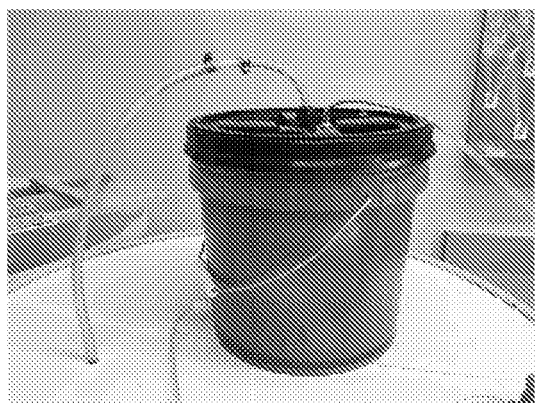
Figure 11B:
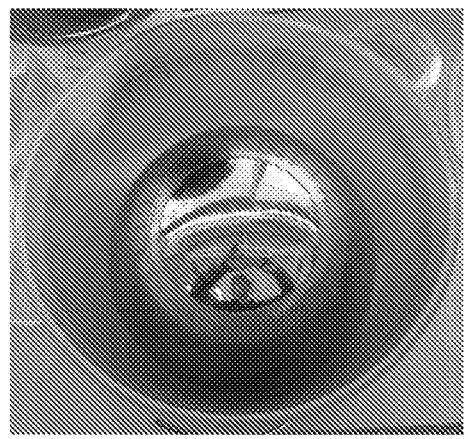
Figure 11C:
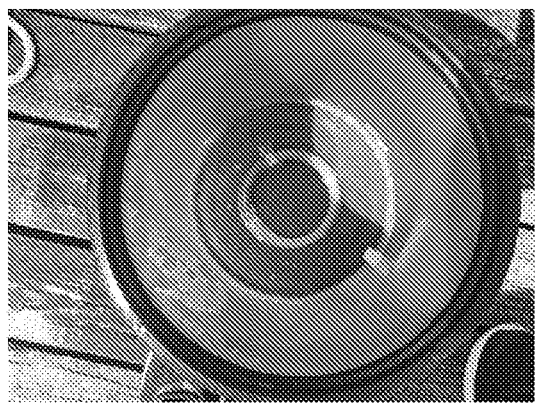
Figure 11D:
Figure 11E:
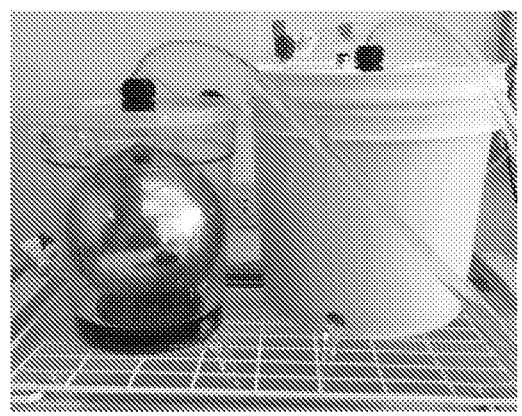
Figure 11F:
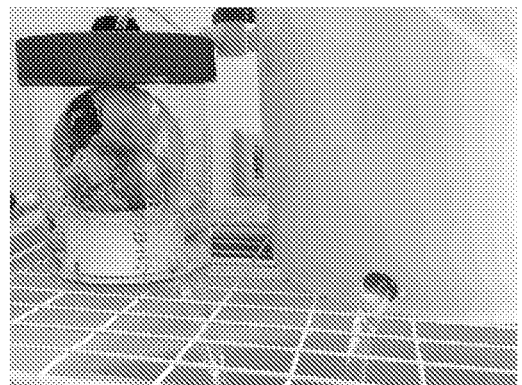

FIG. 9 shows a performance comparison of the equilibrators having an 8-inch diameter spherical equilibration member with the equilibrator having a 10-inch dimeter equilibration member over a 6-day period. The 10-inch and 8-inch equilibrators were connected to the gas analyzer repeatedly and over a wide variety of $CO_2$ concentrations ranging from well below atmospheric concentrations to over 1200 ppmv. In all instances, the 8-inch and 10-inch equilibrators were in near exact agreement of one another.

Example 2. Comparison of Equilibrators with 20 and 9 cm Diameter Equilibration Members The experiment described in Example 1 was repeated using the first equilibrator from Example 1 with an equilibration member having a diameter of about 20.3 cm (about 8 inches) and a chamber volume of about 7.57 liters (about 2 gallons). For this example the second equilibrator had a spherical equilibration member about 9.4 cm (3.7 inches) in diameter and a VRC chamber with a volume of about 1 liter (0.26 gallons). As in Example 1, the resulting measurements show a very high degree of agreement between the two equilibrators.

These and a variety of other tests of the falling film liquid-gas equilibrators described herein across broad ranges of gas (e.g., $CO_2$) concentrations, liquid (e.g., water) and carrier gas (e.g., air) flow rates indicate that falling film equilibrators as described herein have the ability to produce consistent, precise, and accurate dissolved gas measurement (e.g., dissolved $pCO_2$ measurements) even across significantly different equilibrator dimensions. The convergence of the test results using equilibrators of different size suggests that complete equilibration is achieved in each case, as opposed to some arbitrary level(s) of incomplete air-water equilibration.

Example 3. Test of Equilibrator Accuracy—Equilibrium Measurements of Water Enriched with Standard Gas $CO_2$/Air Mixtures A 9 cm diameter equilibrator with a VRC chamber with a volume of about 1 liter (0.26 gallons) was attached via water- and air-tight connectors to a 5-gallon water chamber such that the system was fully closed off from the surrounding ambient atmosphere. The water chamber was enriched by bubbling the water with a certified standard $CO_2$/air mixture. Once the water chamber was fully enriched with the standard gas, the gas was turned off and the equilibrator was turned on. Enriched water was pumped over the equilibrator member, forming a falling film, and then drained back into the enriched water chamber. Equilibration was fully achieved after 9 minutes of run time (5 τ) and the equilibrator headspace $CO_2$ concentration was measured as 7578±12.2 ppmv (mean±1 SD, n=29). This result agreed closely with the certified standard gas nominal concentration (7579 ppmv±1%), and equilibration remained stable for 30 additional minutes, until the equilibrator was turned off. This result indicates that the 9 cm diameter equilibrator equilibrates both quickly and fully (i.e., a stable equilibration with a known target standard was attained by the previously measured time constants.

We claim:
1. An apparatus comprising:
    a chamber comprising an outer wall that is disposed substantially symmetrically about a central axis, the outer wall defining the interior surface of the chamber, the exterior surface of the chamber, and space within the chamber;
    an equilibration member within the chamber having an equilibration member surface, an axis of rotation, and a bisecting plane perpendicular to the axis of rotation positioned at the midpoint of the equilibration member's axis of rotation;
    the equilibration member being positioned within the chamber such that its axis of rotation and the central axis of the chamber coincide or substantially coincide;
    the chamber, the exterior surface of the chamber, the interior chamber wall, the equilibration member within the chamber, and the space within the chamber being divided into an upper portion above the bisecting plane and a lower portion below the bisecting plane;
    the space within the upper portion of the chamber being in liquid (fluid) and gas communication with the space within the lower portion of the chamber via one or more gaps between the equilibration member and the chamber wall;

a liquid inlet located in the upper portion of the chamber positioned such that a liquid introduced into the chamber from the liquid inlet contacts the upper portion of the outer surface of the equilibration member;

a liquid outlet located in the lower portion of the chamber positioned to permit outflow of some or all of the liquid introduced into the chamber that collects in the lower portion of the chamber by gravity;

a gas inlet located in the wall of the lower portion of the chamber; and a gas outlet located in the wall of the upper portion of the chamber;

wherein at least a section of the upper portion of the chamber wall is removably-resealable to the remainder of the upper surface and/or the outer wall.

2. The apparatus of claim 1 wherein the equilibration member is selected from the group consisting of: a spheroid; an ellipsoid, an ovoid; a fusiform shape; a hemisphere; a hemiellipsoid; a hemiovoid; a domed frustum; a series (two, three, four, or more) of spheres or disks aligned along the central axis; a column; a column having one, two, three, four, or more spiral grooves; a column having sinusoidal oscillating sides; a cone having one, two, three, four, or more spiral grooves; and a cone having sinusoidal oscillating sides.

3. The apparatus of claim 2 wherein the interior and/or exterior surface of the chamber is substantially in the form of a vertical right cylinder, a sphere, an ellipsoid, or an ovoid.

4. The apparatus of claim 3, wherein the chamber is a substantially vertical right cylinder (VRC) wherein the wall forms an upper and a lower surface positioned substantially perpendicular to the central axis of the chamber.

5. The apparatus of claim 4, wherein the section of the upper portion of the wall that is removably-resealable forms a lid on the chamber,
wherein when the chamber is a VRC with an upper surface positioned substantially perpendicular to the central axis of the chamber, the lid comprises all or part of the upper surface.

6. The apparatus of claim 5, wherein the liquid inlet is positioned in the lid.

7. The apparatus of claim 6, wherein the liquid inlet is positioned either at, or proximate to, the central axis.

8. The apparatus of claim 6, wherein, when the chamber is a VRC with a lower surface positioned substantially perpendicular to the central axis of the chamber, the liquid outlet and/or the gas inlet are positioned in the lower surface of the chamber.

9. The apparatus of claim 6, wherein the liquid outlet is positioned in the lower portion of the outer wall of the chamber, wherein the liquid outlet is of an adjustable diameter to accommodate a range of liquid flow rates, and wherein liquid flowing through the outlet creates a seal that limits gas from entering or exiting the equilibrium chamber by way of the liquid outlet thereby forming a self-correcting pressure seal that equalizes the interior and exterior pressure to substantially match ambient barometric pressure.

10. The apparatus of claim 9, wherein the gas inlet is positioned in the wall of the chamber at a level between the bisecting plane of the equilibration member in the chamber and a plane that is perpendicular to the central axis and parallel to a plane passing through the liquid outlet.

11. The apparatus of claim 10, wherein the gas outlet is positioned in the removably-resealable portion of the chamber wall.

12. The apparatus of claim 1, wherein, when the chamber is a vertical right cylinder (VRC), the gas outlet is not located in the removably-resealable portion of the chamber wall.

13. The apparatus of claim 1, wherein the surface of the equilibration member is not porous and/or does not absorb water; and wherein the surface of the equilibration member is hydrophilic.

14. The apparatus of claim 1, wherein the interior surface of the chamber has a contact angle with water greater than about 70°, 80°, 90°, 100°, 110°, 120°, 130°, or 140° at 22° C.; or wherein the interior surface of the chamber has a slide angle with water less than about 30°, 20°, 10°, or 5° at 22° C.

15. The apparatus of claim 1:
further comprising an annular element within the chamber in contact with the lower portion of the chamber and the equilibration member; or
wherein the equilibration member comprises a magnet or a magnetically susceptible material, and wherein the apparatus further comprises a magnet or magnetically susceptible material positioned on or in the chamber wall so as to magnetically engage the equilibration member.

16. The apparatus of claim 1, wherein the volume of the chamber is less than 2.5 times the volume of the equilibration member.

17. A method of determining the amount of a gas or gases of interest present in a liquid comprising the following steps:
i) providing an apparatus of claim 1;
ii) introducing the liquid into the chamber of the apparatus by way of the liquid inlet such that it passes over the equilibration member, thereby forming a film over all or part of the equilibration member's surface, and exits the apparatus by way of the liquid outlet;
iii) directing a carrier gas into the apparatus by way of the gas inlet such that it flows over the equilibration member in a direction that is counter current to the flow of the liquid and exits the chamber of the apparatus by way of the gas outlet;
iv) directing all or part of the gas that exits the chamber to a sensor of an analytical instrument that determines the amount of the gas or gases of interest present in the liquid; and
v) determining the amount of a gas or gases of interest present in the liquid based on the output of the analytical instrument.

18. The method of claim 17, wherein the carrier gas is selected from the group consisting of air, nitrogen, an inert gas, hydrogen, oxygen or a mixture of any thereof; and wherein at least one of the gas or gases of interest is selected from the group consisting of ammonia, $CO_2$, CO, sulfur oxides, nitrogen oxides, methane, ethane, hydrocarbons, halogenated hydrocarbons, chlorofluorocarbons (CFCs), hydrofluorocarbons (HFCs), perfluorocarbons (PFCs), esters, sulfur hexafluoride ($SF_6$), chlorine, bromine, radon, hydrogen sulfide ($H_2S$), HF, HCl, HBr, and HI.

19. The method of claim 17, wherein the gas of interest is $CO_2$.

20. The method of claim 19, wherein the liquid comprises water.

* * * * *